US011033223B2

(12) United States Patent
Ludewig et al.

(10) Patent No.: US 11,033,223 B2
(45) Date of Patent: Jun. 15, 2021

(54) 3D SHOULDER MOTION MEASUREMENT DEVICE AND SCAPULAR ANGLE LOCATOR

(71) Applicant: Regents of the University of Minnesota, Minneapolis, MN (US)

(72) Inventors: Paula Ludewig, Minneapolis, MN (US); Justin Staker, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 223 days.

(21) Appl. No.: 15/581,803

(22) Filed: Apr. 28, 2017

(65) Prior Publication Data

US 2017/0311875 A1 Nov. 2, 2017

Related U.S. Application Data

(60) Provisional application No. 62/329,656, filed on Apr. 29, 2016.

(51) Int. Cl.
*A61B 5/11* (2006.01)
*A61B 5/00* (2006.01)

(52) U.S. Cl.
CPC .......... *A61B 5/4576* (2013.01); *A61B 5/0004* (2013.01); *A61B 5/1121* (2013.01); *A61B 5/1126* (2013.01); *A61B 5/6898* (2013.01); *A61B 5/742* (2013.01); *A61B 2505/09* (2013.01); *A61B 2560/0223* (2013.01); *A61B 2560/0425* (2013.01)

(58) Field of Classification Search
None
See application file for complete search history.

(56) References Cited

U.S. PATENT DOCUMENTS

2009/0322763 A1* 12/2009 Bang .................. G06K 9/00342
345/474
2017/0281074 A1* 10/2017 D'Lima ............... A61B 5/0488

OTHER PUBLICATIONS

"Fitness Trainers and Instructors," Fitness Trainers and Instructors: Occupational Outlook Handbook, U.S. Bureau of Labor Statistics, accessed from https://www.bls.gov/ooh/personal-care-and-service/print-fitness-trainers-and-instructors.htm, accessed on Aug. 17, 2017, 9 pp.
"Occupational Therapists," Occupational Outlook Handbook, U.S. Bureau of Labor Statistics, accessed from https://www.bls.gov/ooh/healthcare/print/occupational-therapists.htm on Aug. 17, 2017, 8 pp.
"Physical Therapists in the US: Market Research Report," IBISWorld, Apr. 2017, 7 pp.
"Profile of Athletic Trainers," National Athletic Trainers' Association, Jul. 2014, 2 pp.

(Continued)

*Primary Examiner* — Eric F Winakur
*Assistant Examiner* — Marjan Fardanesh
(74) *Attorney, Agent, or Firm* — Shumaker & Sieffert, P.A.

(57) ABSTRACT

Examples of systems, devices, and methods as described in this disclosure include a shoulder motion measurement system comprising a mounting device comprising a receptacle configured to hold an electronic device at a fixed orientation relative to a scapula of a patient, wherein the mounting device comprises one or more structures configured for handling by a user when aligning the shoulder motion measurement system against the patient.

17 Claims, 26 Drawing Sheets

(56) References Cited

OTHER PUBLICATIONS

"What is WCPT?," World Confederation for Physical Therapy, accessed from http://www.wcpt.org/what-is on Aug. 17, 2017, 2 pp.
Barzouhi et al., "Magnetic Resonance Imaging in Follow-up Assessment of Sciatica," The New England Journal of Medicine, Mar. 14, 2013, 9 pp.
Borstad et al., "Comparison of scapular kinematics between elevation and lowering of the arm in the scapular plane," Clinical Biomechanics, Elsevier, Sep. 16, 2002, 10 pp.
Brochard et al., "Double Calibration: An accurate, reliable and easy-to-use method for 3D scapular motion analysis," Journal of Biomechanics, vol. 44, Issue 4, Elsevier, Feb. 2011, 4 pp.
Hickey et al., "Accuracy and reliability of observational motion analysis in identifying shoulder symptoms," Manual Therapy, Elsevier, May 8, 2006, 8 pp.
Johnson et al., "Estimates of Direct Health Care Expenditures Among Individuals with Shoulder Dysfunction in the United States," http://www.asset-usa.org/Abstracts/Johnson_Crossley_Oneil_Al-Kakwani.html accessed on Aug. 17, 2017, 1 pp.
Johnson et al., "New Method to Assess Scapular Upward Rotation in Subjects With Shoulder Pathology," Journal of Orthopaedic & Sports Physical Therapy, Feb. 2001, 9 pp.
Krief et al., "Shoulder Pain and Disability: Comparison with MR Findings," Musculoskeletal Imaging, American Roentgen Ray Society, May 2006, 6 pp.
Lawrence et al., "Comparison of 3-Dimensional Shoulder Complex Kinematics in Individuals With and Without Shoulder Pain, Part 2: Glenohumerial Joint," vol. 44, No. 9, Journal of Orthopaedic & Sports Physical Therapy, Sep. 2014, 13 pp.
Ludewig et al., "Motion of the Shoulder Complex During Multiplanar Humerial Elevation," Journal of Bone and Joint Surgery, vol. 91-A, No. 2, Feb. 2009, 12 pp.
Ludewig et al., "Shoulder impingement: Biomechanical considerations in rehabilitation," 3rd International Conference on Movement Dysfunction, vol. 16, Issue 1, Feb. 2011, 7 pp.
Ludewig et al., "Translations of the Humerus in Persons with Shoulder Impingement Symptoms," Journal of Orthopaedic & Sports Physical Therapy, Iowa Research Online, Jun. 1, 2002, 13 pp.
McClure et al., "A Clinical Method for Identifying Scapular Dyskinesis, Part 1: Reliability," Journal of Athletic Training, vol. 44, No. 2, Apr. 2009, 5 pp.
McWilliams, "Healthcare Information Technology," A BCC Research Healthcare Report, Mar. 2015, 5 pp.
Scibek et al., "Validation of a New Method for Assessing Scapular Anterior-Posterior Tilt," The International Journal of Sports Physical Therapy, vol. 9, No. 5, Oct. 2014, 13 pp.
Shaheen et al., "Tracking the scapula using the scapula location with and without feedback from pressure-sensors: A comparative study," Journal of Biomechanics, May 2011, 4 pp.
Sigmundsson et al., "Correlation between disability and MRI findings in lumbar spinal stenosis, A prospective study of 109 patients operated on by decompression," Acta Orthopaedica, Apr. 5, 2011, 7 pp.
Sobush et al., "The Lennie Test for Measuring Scapular Position in Healthy Young Adult Females: A Reliability and Validity Study," Journal of Othopaedic & Sports Physical Therapy, vol. 23, No. 1, Jan. 1996, 12 pp.
Struyf et al., "Clinical assessment of the scapula: a review of the literature," BMJ Publishing Group, Jul. 21, 2012, 9 pp.
Su et al., "Scapular Rotation in Swimmers with and without Impingement Syndrome: Practice Effects," Medicine & Science in Sports & Exercise, Jul. 2004, 7 pp.
Tate et al., "A Clinical Method for Identifying Scapular Dyskinesis, Part 2: Validity," Journal of Athletic Training, vol. 44, No. 2, Apr. 2009, 9 pp.
Timmons et al., "Scapular Kinematics and Subacromial-Impingement Syndrome: A Meta-Analysis," Journal of Sport Rehabilitation, vol. 21, Article No. 4, Nov. 2012, 17 pp.
Van Andel et al., "Recording scapular motion using an acromion marker cluster," Gait and Posture, vol. 29, Jul. 23, 2008, 6 pp.
Van Den Noort et al., "Reliability and precision of 3D wireless measurement of scapular kinematics," Medical and Biological Engineering & Computing, Springer, Nov. 2014, 11 pp.
Wassinger et al., "Clinical Measurement of Scapular Upward Rotation in Response to Acute Subacromial Pain," Research Report, Journal of Orthopaedic & Sports Therapy, vol. 43, No. 4, Apr. 2013, 5 pp.
Tucker et al., "Reliability and Validity of Measuring Scapular Upward Rotation using an Electrical Inclinometer," Journal of Electromyography and Kinesiology, Elsevier, Feb. 2012, 5 pp.
Ogston et al., "Differences in 3-Dimensional Shoulder Kinematics Between Persons with Multidirectional Instability and Asymptomatic Controls," The American Journal of Sports Medicine, vol. 35, No. 8, Apr. 2007, 10 pp.
Braman et al., "In Vivo Assessment of Scapulohumeral Rhythm During Unconstrained Overhead Reaching in Asymptomatic Subjects," J Shouldr Elbow Surg., NIH Public Access Author Manuscript, Nov. 1, 2010, 16 pp.
Braman et al., "Shoulder Impingement Revisited: Evolution of Diagnostic Understanding in Physical Therapy and Orthopaedic Surgery," Medical and Biological Engineering & Computing, vol. 52, Issue 3, Mar. 2014, 6 pp.
Ludewig et al., "Three-Dimensional Scapular Orientation and Muscle Activity at Selected Positions of Humeral Elevation," Journal of Orthopaedic & Spots Physical Therapy, vol. 24, No. 2, Aug. 1996, 11 pp.
Ludewig et al., "Three-Dimensional Clavicular Motion During Arm Elevation: Reliability and Descriptive Data," Journal of Orthopaedic & Sports Physical Therapy, vol. 34, No. 3, Mar. 2004, 10 pp.
"Letter to the Editor-in-Chief," Journal of Orthopaedic & Sports Physical Therapy, vol. 43, No. 9, Sep. 2013, 4 pp.
Lawrence et al., "Comparison of 3-Dimensional Shoulder Complex Kinematics in Individuals With and Without Shoulder Pain, Part 2: Glenohumeral Joint," Research Report, Journal of Orthopaedic & Sports Physical Therapy, vol. 44, No. 9, Sep. 2014, 13 pp.
Lawrence et al., "Comparison of 3-Dimensional Shoulder Complex Kinematics in Individuals with and Without Shoulder Pain, Part 1: Sternoclavicular, Acromioclavicular, and Scapulothoracic Joints," J. Orthop Sports Phys Therapy, HHS Public Access—Author Manuscript, Dec. 20, 2015, 19 pp.
Lawrence et al., "Effect of Glenohumeral Elevation on Subacromial Supraspinatus Compression Risk During Simulated Reaching," Journal of Othopaedic Research, Oct. 2017, 9 pp.
Ludewig et al., "Relative Balance of Serratus Anterior and Upper Trapezius Muscle Activity During Push-Up Exercises," The American Journal of Sports Medicine, vol. 32, No. 2, Mar. 2004, 10 pp.
Ludewig et al., "The Association of Scapular Kinematics and Glenohumeral Joint Pathologies," Clinical Commentary—Journal of Orthopaedic and Sports Physical Therapy, vol. 39, No. 2, Feb. 2009, 29 pp.
Ludewig et al., "Alterations in Shoulder Kinematics and Associated Muscle Activity in People with Symptoms of Shoulder Impingement," American Physical Therapy Association, vol. 80, No. 3, Mar. 2000, 17 pp.
Ludewig et al., "Comparison of scapular local coordinate systems," Clin Biomech, NIH-PA Author Manuscript, Jun. 1, 2011, 15 pp.
Phadke et al., "Comparison of Glenohumeral Motion Using Different Rotation Sequences," J. Biomech, NIH Public Access Author Manuscript, Feb. 24, 2012, 15 pp.
Hamming et al., "The accuracy of measuring glenohumeral motion with a surface humeral cuff," J. Biomech, NIH Public Access Author Manuscript, Apr. 30, 2013, 22 pp.
Nawoczenski et al., "Clinical Trial of Exercise for Shoulder Pain in Chronic Spinal Injury," Research Report, Physical Therapy, vol. 86, No. 12, Dec. 2006, 15 pp.
Staker et al., "Comparing Helical and Pivot Methods for Locating the Humeral Head Center to Describe In-Vivo Humeral Head Translations," 10th Conference of the International Shoulder Group, Jul. 13-15, 2014, pp. 107-108, 3 pp.

(56) References Cited

OTHER PUBLICATIONS

Teece et al., "Three-Dimensional Acromioclavicular Joint Motions During Elevation of the Arm," J. Orthop Sports Phys. Therapy, NIH Public Access Author Manuscript, Oct. 10, 2009, 23 pp.

Ludewig et al., "Effects of a home exercise programme on shoulder pain and functional status in construction workers," Occupational & Environmental Medicine, vol. 60-11, Nov. 2003, 9 pp.

Staker et al., "Three-dimensional kinematics of shoulder laxity examination and the relationship to clinical interpretation," International Biomechanics, vol. 4, No. 2, 77-85, published online http://www.tandfonline.com/action/journalinformation?journalcode+tbbe20 on Dec. 15, 2017, 10 pp.

Staker et al., "Movement-Based Biomechanical Examination Following a 3-Year case of Scapular Dyskinesia," Journal of Orthopaedic and Sports Physical Therapy, vol. 45, No. 1, Abstract, Jan. 2015, OPO2290, A106, 1 p.

Dragseth et al., "Effects of Feedback Types on Sternoclavicular Elevation and Upper Trapezius Activation in Persons with Shoulder Pain," Journal of Orthopaedic and Sports Physical Therapy, vol. 45, No. 1, Abstract, Jan. 2015, OPO1107, A78, 1 p.

* cited by examiner

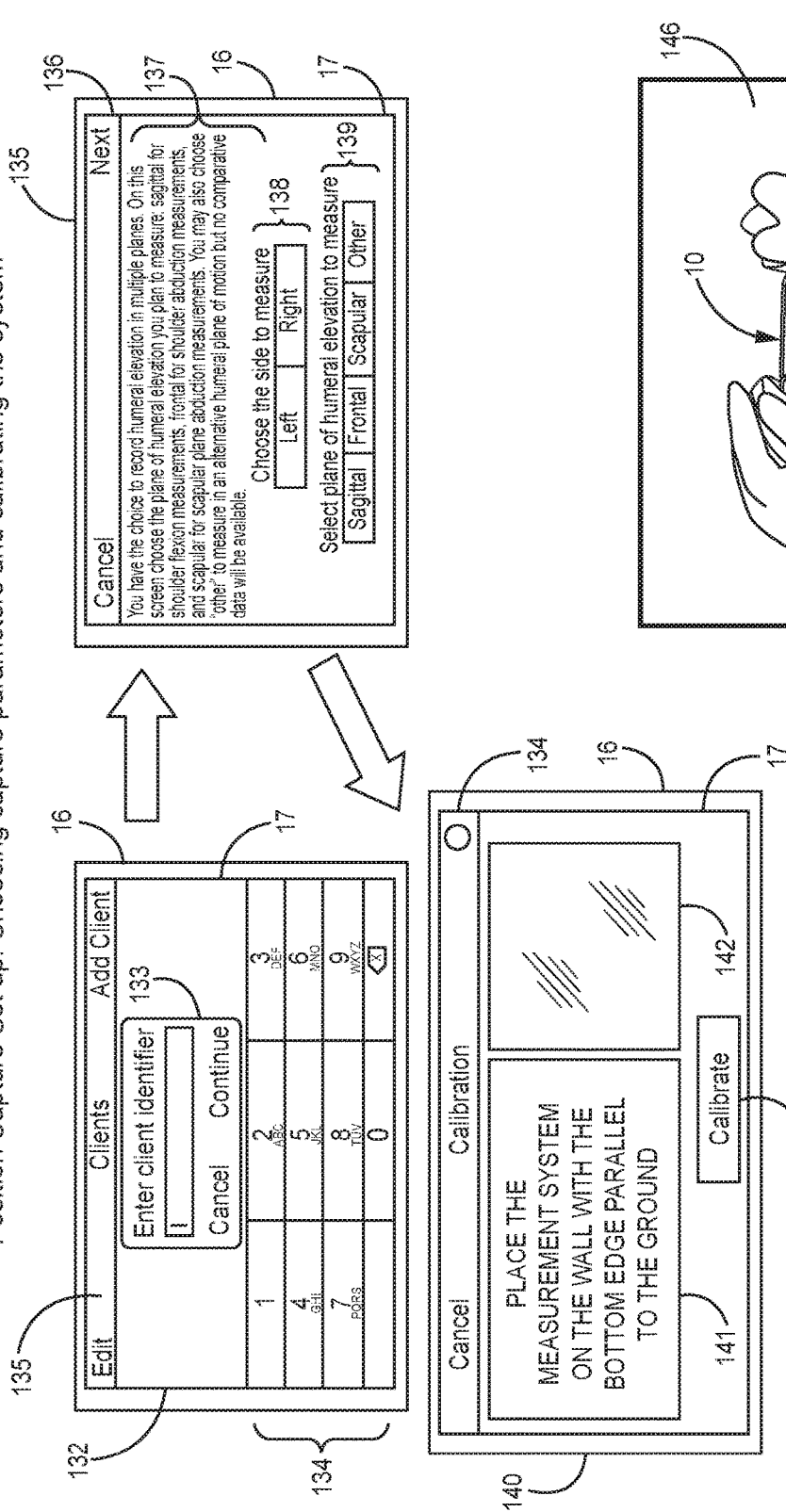
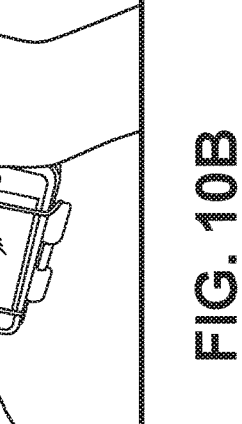
FIG. 10A
FIG. 10B

3D SHOULDER MOTION MEASUREMENT DEVICE AND SCAPULAR ANGLE LOCATOR

CROSS-REFERENCE TO RELATED APPLICATION

This application claims the benefit of U.S. Provisional Application Ser. No. 62/329,656, filed Apr. 29, 2016, the entire content of which is incorporated by reference herein in its entirety.

STATEMENT REGARDING FEDERALLY SPONSORED RESEARCH OR DEVELOPMENT

This invention was made with government support under 1U01-HL127479-01 awarded by the National Institutes of Health. The government has certain rights in the invention.

TECHNICAL FIELD

The disclosure relates to devices for classification and monitoring of rehabilitation progress of musculoskeletal injuries or neurologic movement disorders, such as shoulder joint dysfunctions.

BACKGROUND

Musculoskeletal and neuromuscular movement disorders affect nearly every individual at some point in their lifetime, with treatment costs reaching hundreds of billions of dollars annually. Optimal diagnosis and treatment of these disorders requires the ability to objectively measure three-dimensional motion over time, because most of these pathologies originate with movement. However, most musculoskeletal health diagnoses currently are focused on identification of specific tissue pathologies and often include expensive imaging, such as MRI. Increasing evidence suggests identification of these tissue pathologies is not highly related to patient function or pain. Unlike surgery, where imaging data directs a surgical intervention, rehabilitation providers do not have easy to use non-invasive clinical tools to diagnose movement conditions.

SUMMARY

In general, this disclosure describes examples of a measurement system for tracking three-dimensional angles of the scapula during arm movement. In one example, the system may be a handheld shoulder motion measurement system for mounting and utilizing a smartphone application for tracking the three-dimensional angles of the scapula during arm movement. The system may be cost-effective by pairing readily available smart-phone sensor technology with a simple tracking attachment and a mobile software application to guide clinicians, motivate patients, and improve outcomes.

Example shoulder motion measurement systems described herein offer cost-effective, accurate, precise, and objective three-dimensional motion measurement for clinicians treating patients or athletes with shoulder pain or motion disorders. Accurate, precise, and objective classification allows proper diagnosis and treatment planning, objective tracking of progress over time within and between providers, and improved outcomes to patients at lower cost to insurers.

In one example, the disclosure is directed to a shoulder motion measurement system comprising: a mounting device comprising a receptacle configured to hold an electronic device at a fixed orientation relative to a scapula of a patient, wherein the mounting device comprises one or more structures configured for handling by a user when aligning the shoulder motion measurement system against the patient.

In another example, the disclosure is directed to a method for measuring motion of a scapula using a shoulder motion measurement system, the method comprising: securing an electronic device into a receptacle of a mounting device, the electronic device configured to measure and display a plurality of positions along a three-dimensional (3D) motion of the scapula of a patient, positioning a backside of the mounting device including the mobile device against a back of the patient and aligned with a scapula of the patient; and actuating the mobile device to measure one or more degrees of rotation associated with the scapula of the patient when the arm of the patient associated with the scapula resides in a first defined position.

In another example, the disclosure is directed to a non-transitory computer-readable storage medium having stored thereon instructions that when executed cause one or more processors to: receive an input signal indicating that an electronic device positioned and aligned to the scapula of a patient is to take one or more measurements corresponding to one or more degrees of rotation associated with a scapula of the patient; control one or more motion sensors to generate sensor output signals corresponding to measured values associated with the one or more degrees of rotation of the scapula of the patient; receive the generated sensor output signals; and process the sensor output signals to generate data associated with the one or more degrees of rotation of the scapula.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 10A-10B illustrate an example process by which a user interacts with a shoulder motion measurement system according to various techniques described in this disclosure.

DETAILED DESCRIPTION

Figure 1A:
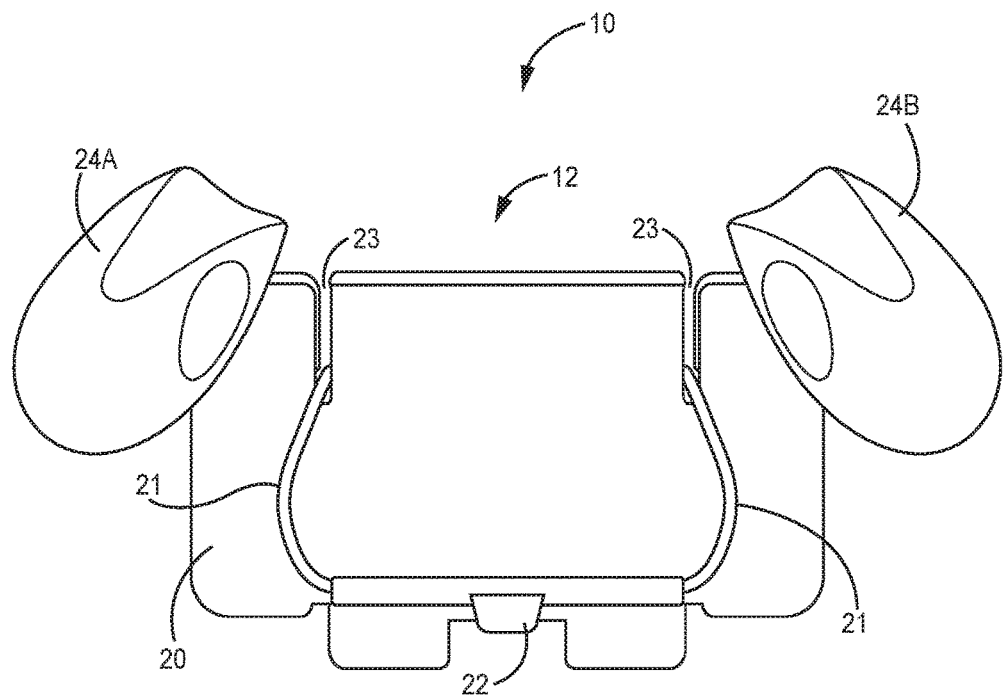
FIG. 1A is a diagram illustrating one example of a three-dimensional (3D) shoulder motion measurement system in accordance with various techniques described in this disclosure.
Figure 1A:
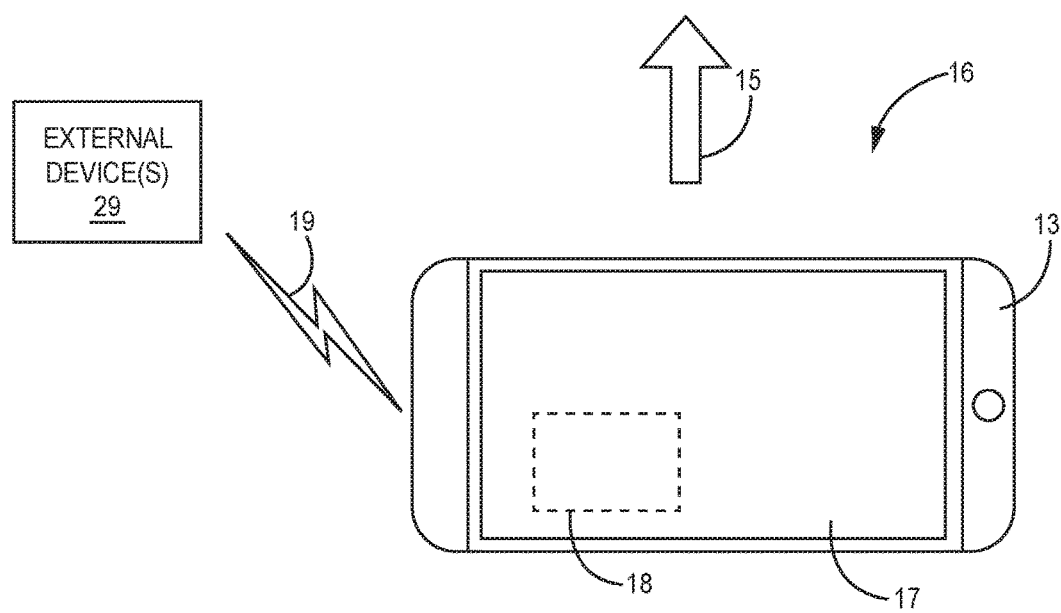

The present disclosure describes examples of a handheld shoulder motion measurement system for mounting and utilizing an application operating on an electronic device, such as a smartphone, for tracking the three-dimensional angles of the scapula(s) in patients, who are generally human patients, during arm movement.

Objective measures of scapular position are important to facilitate measurement of joint position for diagnosis and treatment of musculoskeletal injuries. Current technology for making these measurements is generally based on the use of digital inclinometers, which can relay only one dimensional information to the user. These devices typically only display the data in real time, preventing review and interpretation by the clinician or researcher. Digital inclinometers are expensive and limited to only measuring one of three angles of scapular motion relative to gravity only, leading to measurement errors.

Examples are described herein of a mounting device and associated software application(s) that takes advantage of a mobile computing devices' (e.g., smartphones') capabilities to measure three angles at a time and also utilizes the clinician's palpatory skills. Typically, devices that measure the scapula in three angles are used primarily in research and are expensive, have very limited portability, and require special knowledge to interpret the results. For example, electromagnetic based research devices are not hand-held devices, and are typically limited in range by connected cables between sensor units and a computer. Commercially available inertial measurements systems and the electromagnetic based research devices typically use short range wireless communication methods, such as Bluetooth®, to provide communications back to a desktop or laptop computer for use in either real-time visualization or processing. Camera based motion analysis systems require dedicated space and wired connections to a desktop device. The devices are usually placed on the landmarks with blunt probes, likely leading to measurement error. The devices described herein may take advantage of the sensitivity of the clinician or researcher's ability to palpate landmarks related to the patient's scapula to improve accuracy. Additionally, the ubiquitous nature of electronic devices, such as smartphones, avoids the need to purchase an additional, expensive inclinometer.

For example, a mobile application executing on a mobile device is paired with a physical mobile device handle (e.g. a mounting device) as described herein, that is designed to maximize accuracy of measurement for shoulder positions. The system is designed to offer cost-effective, accurate, precise, and objective three-dimensional motion measurement for clinicians treating patients or athletes with shoulder pain or motion disorders. Accurate, precise, and objective classification can allow proper diagnosis and treatment planning, objective tracking of progress over time within and between providers, and improved outcomes to patients at lower cost to insurers. The device is cost-effective by pairing readily available technology, for example as would be normally be provided by smart-phone sensor technology, with a low-cost tracking attachment and a mobile software application to guide clinicians, motivate patients, and potentially improve outcomes.

As described herein, the physical design of the handle is planned to maximize accuracy of measurement, including placement and stabilization of fingers relative to important bony landmarks, and ergonomic grip to stabilize the electronic device while taking measurements, and anthropometrically planned dimensions to most accurately stabilize the electronic device on a variety of patient shoulder physical dimensions. The accompanying mobile application is designed with custom software code to utilize the three-dimensional sensors of a mobile device (i.e. Apple iPhone®, Apple iPod Touch®, Android systems) to capture accurate three-dimensional position information of the bone being measured.

Current clinical standard of care for movement assessment of the scapula is primarily visual observation. This approach is inadequate because it is subjective between examiners, particularly those with differing levels of clinical experience, it is limited to identifying presence or absence of overall scapular movement abnormalities, it does not allow objective tracking of progress, and it does not allow adequate diagnosis or clinical decision making.

Various implementations of the device described herein may address the unmet customer needs for 1) an objective, accurate, cost-effective, and easy to use tool to classify three-dimensional shoulder movement disorders, 2) ability to diagnostically direct treatment, and 3) reliable tracking of patient progress over time. Currently used imaging based systems are highly accurate for tissue pathology identification, but are invasive and time-intensive for the patient, provide limited measures for the clinician (static positional), and are expensive to the health system due to required clinical resources and personnel. These scans also only provide information on tissue pathology, not the movement abnormalities which are the focus of rehabilitation providers' treatments, and fundamental to successful patient outcomes.

Simple clinical tools such as inclinometers are available, but these are rarely used by clinicians for shoulder motion measurement as they can be: 1) difficult to use accurately during shoulder movements; 2) do not produce substantive visual or graphical outputs; 3) are limited to a single angle relative to gravity; and 4) may cost thousands of dollars for dual digital systems.

In contrast, the devices and techniques described herein are designed to address each aspect of the current unmet needs in objectively identifying, longitudinally tracking, and successfully treating shoulder movement disorders. Moreover, the described devices and techniques may improve competence and confidence in shoulder motion measurement, particularly for novice and less experienced practitioners. Further, the described device and techniques may cost significantly less than competitors. The devices and techniques described herein address the unmet customer needs for 1) an objective, accurate, cost-effective, and easy to use tool to classify 3-dimensional shoulder movement disorders, 2) ability to diagnostically direct treatment, and 3) reliable tracking of patient progress over time.

Although described with respect to shoulder diagnosis and therapy, similar devices suitable for receiving a mobile device may be configured and applied to other joint motions, resulting in a suite of simple measurement devices and associated mobile applications for the diagnosis and guided treatment of musculoskeletal and neuromuscular movement disorders.

FIG. 1A is a diagram illustrating one example of a three-dimensional (3D) shoulder motion measurement system 10. As shown in FIG. 1A, system 10 includes a mounting device 12 including grips 24A, 24B, and a receptacle 20, the receptacle 20 of mounting device 12 arranged to receive and to secure in place at least partially within receptacle 20 a programmable electronic device 16, as indicated by arrow 15 in FIG. 1A. Electronic device 16 is not limited to any particular type of device, and may include any type of programmable electronic device, including a mobile device such as a smartphone, that is configured have one or more shoulder motion measurement application(s) downloaded to the device, and is capable of then running the downloaded application(s) to perform the functions and to provide the features ascribed to system 10 and/or any other features and functions described throughout this disclosure associated with motion measurement systems, devices, and techniques.

In the example shown in FIG. 1A, electronic device 16 is a smartphone comprising a housing 13 and a display 17, the display visible at least from a front side of the housing 13. Electronic device 16 further includes circuitry 18, such as one or more processor(s) and memory, that may be configured to store one or more applications related to shoulder motion measurements in the memory, and to execute these application(s), using the one or more processors of circuitry 18, in order to perform any of features and functions related to the shoulder motion measurement systems ascribed to system 10, and/or any other features and functions of the shoulder motion measurement system described throughout this disclosure, and any equivalents thereof. Examples of circuitry 18 included within electronic device 16 may include any one or a combination of the devices and circuits illustrated and described with respect to electronic device 120 in FIG. 9.

Referring again to FIG. 1A, the one or more applications related to shoulder motion measurements may be downloaded to electronic device 16, for example via a communication link 19, from one or more external devices 29. External devices 29 are not limited to any particular type of device or devices, and may include a computer, such as but not limited to a laptop computer, or a computer network including a server, or for example one or more devices communicatively coupled via the Internet to a website location configured to provide the downloadable applications. In various examples, communication link 19 is a wireless communication link, using a communication format such as Bluetooth or via WiFi. However, communication link 19 used to download the one or more applications to electronic device 16 is not limited to any particular communication format, and may include use of any communication format(s) that may be utilized to download applications to an electronic device, such as electronic device 16. In various examples, communication link 19 may be a wired form of a communication link, such as provided through a wired connected coupled to a Universal Serial Bus (USB) or other port on electronic device 16. Wired communications links used to download application(s) to electronic device 16 are not limited to any particular form of wired communication link, and may include any type of wired communication link that may be used to download applications to an electronic device, as would be understood by one of ordinary skill in the art.

Once the one or more applications have been downloaded to the electronic device 16, the shoulder motion measurement system 10 may utilize the electronic device's sensor technology in conjunction with mounting device 12 and the downloaded application(s) executing on electronic device 16, to aid users in identifying and successfully treating shoulder movement disorders. The term "user" as provided in this disclosure may include physicians, technicians, and/or clinicians who are using the shoulder motion measurement systems described throughout this disclosure, to perform any of the procedures, and to operate the system to provide the functions ascribed to the shoulder measurement systems throughout this disclosure, and any equivalents thereof. Various features and functions ascribed to these systems may be operated by and provided to a patient, with or without the assistance or presence of another user, in which case the general term "user" may also apply to the patient on which these measurement procedures are, have been, or are intended to be performed on using these systems, and any equivalents thereof.

As shown in FIG. 1A, mounting device 12 includes a receptacle 20 that may be sized and shaped to receive electronic device 16 of various sizes, for example various sizes of smartphones, and to secure the electronic device in a fixed orientation and position relative to a frame of reference of the mounting device 12. In some examples, mounting device 12 includes one or more slots 23 formed in the receptacle 20 for receiving one or more elastic bands 21. Elastic bands 21 may be positioned to extend through slots 23 and to extend across receptacle 20 to clip 22. Elastic bands 21 may be arranged to be resiliently stretched to extend over one or more surfaces of electronic device 16 once the electronic device is received and positioned at least partially within receptacle 20. Once electronic device 16 has been received in receptacle 20, elastic bands 21 may be arranged to extend from slots 23, and for example over the front side of electronic device 16 that includes display 17, to clip 22 in order to secure the electronic device in place at least partially within receptacle 20 while still allowing display 17 to be visible.

Once electronic device 16 has been inserted into receptacle 20 and elastic bands 21 have been extended over the electronic device, clip 22 may be operated to tighten the elastic bands 21, and therefore to further secure electronic device 16 in a fixed position and at least partially within receptacle 20. Mounting device 12 further includes a left grip 24A and a right grip 24B by which the user holds and positions measurement system 10 relative to a patient. In the example shown, grips 24A and 24B are ergonomically designed for most common anthropometric hand dimensions, and aligned to direct the fingers of the user most accurately to specific anatomical locations based on a small database of expected dimensions and range of variation. In some examples, the grips are designed to ergonomically match the hand grip of the "50th percentile" of users, and biomechanically sound wrist and finger positions for precision grip. This provides stable control of the system while taking measurements.

Grips 24A-24B comprise contoured surfaces having grooves that are specifically configured and spaced to direct the fingers most accurately to the anatomical landmarks (root of scapular spine and posterior lateral acromion) that are most accurately palpable to track scapular motion, even in the presence of active muscle contraction of surrounding musculature. Grip contours of grips 24A-24B are ergonomically designed to fit natural and biomechanically sound precision grip.

Through the shoulder motion measurement system 10 and the one or more applications downloaded to electronic device 16, a quantifiable clinical method for measuring subtle abnormalities in shoulder motion is possible. The accurate detection of movement abnormalities improves diagnostic accuracy, and is a prerequisite to providing focused and cost effective treatment. Example implementations of the system 10 provide a point of care clinical decision support system (CDSS). The shoulder motion measurement system 10 integrates the patient's movement data to provide targeted diagnostic information and treatment recommendations based on current evidence. As a result, shoulder motion measurement system 10 provides a new standard of care for shoulder movement diagnoses and treatment.

The examples of mounting device 12 as described throughout this disclosure, for example with respect to FIGS. 1A-1E, are not limited to being made of any particular type of material, and in some examples is a polymeric material. In some examples, mounting device 12 may be formed of vinyl, such as a polyvinylchloride, in either a rigid or a plasticized, more flexible arrangement. In some examples, various portions of mounting device 12, such as the backplate area that forms receptacle 20 and grips 24A-24B, may be made of a same material. In other examples, different portions of mounting device 12 may be formed of different materials. In some examples, these different portions may be formed as a single piece, or may be formed initially as separate pieces, and assembled to form the mounting device 12. In various examples, bands 21 may be formed of a polymeric and elastic material, such as an elastomer, for example using a natural or synthetic rubber or silicone.

Figure 1B:
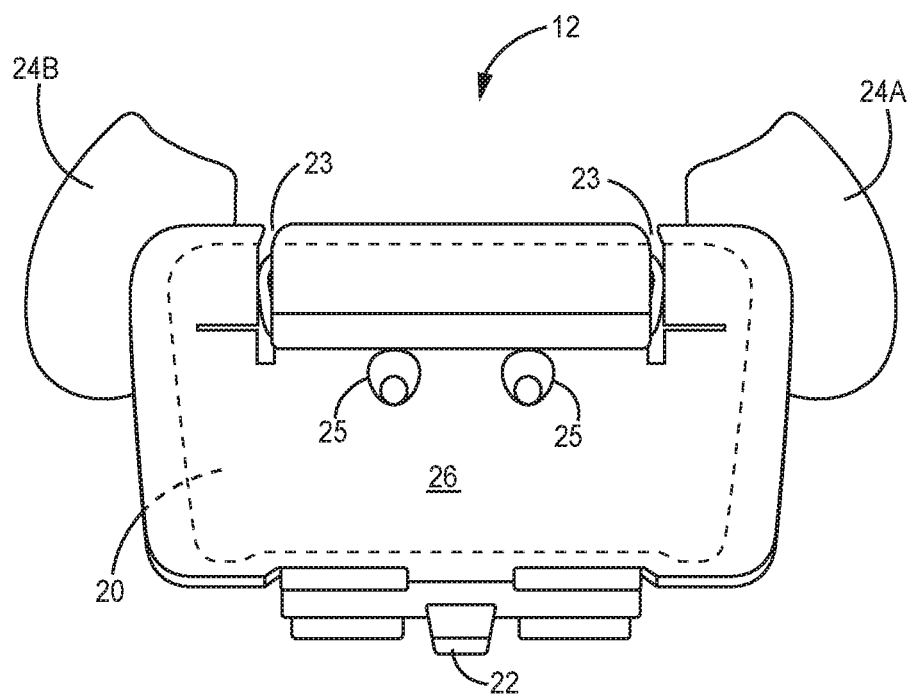
FIG. 1B is a diagram illustrating a backside view of an example of the mounting device of the 3D shoulder motion measurement system illustrated in FIG. 1A.

FIG. 1B is a diagram illustrating a backside view of an example of the mounting device 12 of the 3D shoulder motion measurement system 10 illustrated in FIG. 1A. As shown in FIG. 1B, the backside of mounting device 12 includes a back surface 26 that is a substantially planar surface across the central portions of the surface, and forms an exterior surface of mounting device 12 that is opposite and substantially parallel to one or more corresponding surfaces that form receptacle 20. The material forming mounting device 12 that is provided between the receptacle 20 and the back surface 26 provides a layer of material having a thickness and that provides the bottom, and in some examples the sides, for the receptacle 20.

Figure 3:
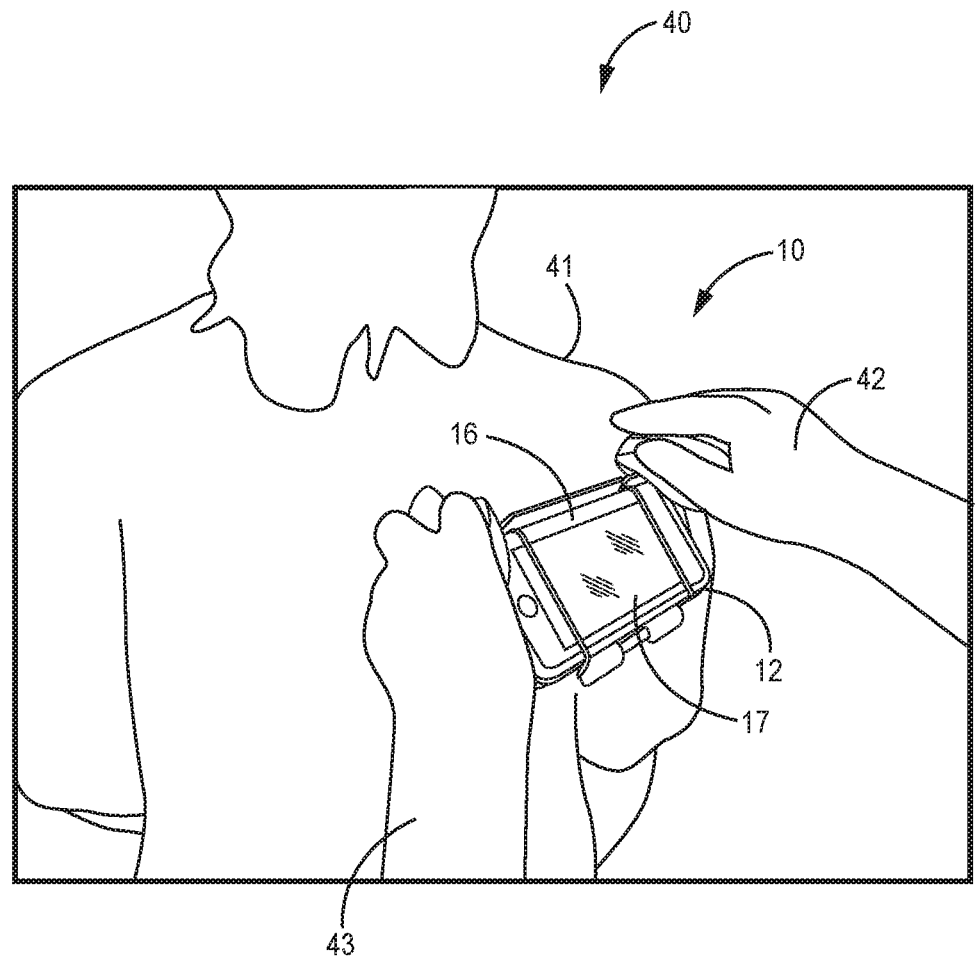
FIG. 3 is a diagram illustrating an example of a measurement system aligned to a scapula of a patient in accordance with various techniques described in this disclosure.

As further described herein, the back surface 26 may be held against a patient's scapula during a diagnostic procedure, as illustrated and described for example with respect to FIG. 3. As shown in FIG. 1B, posterior protrusions 25, or "feet" on the mounting device 12 are positioned on the back surface 26 to allow the user to stabilize the mounting device 12 against the shoulder blade of the patient on which the procedure is being performed. In various examples, a stabilizing effect may be provided by having the protrusions 25 brought into contact with some portion of the patient's back, as use of these protrusions 25 during the procedure may enhance the accuracy of the measurements taken, for example when measuring the full three-dimensional position or motion of the scapula of the patient. In various examples, the protrusions 25 have dimensions that are designed in relation to grips 24A-24B to optimize the clinician's wrist position angle when performing a measurement procedure on the patient using mounting device 12. The protrusions 25 may be configured to allow use for a wide range of scapular sizes, and may be used for procedures involving both left and right sides of the patient. The protrusions 25 in some examples allow the user to stabilize the mounting device 12 against the body of the scapula even in the presence of surrounding musculature contraction. The dimensions of protrusions 25 may reduce or minimize any need to adjust wrist or finger position to comfortably and accurately stabilize the mounting device 12 against the body of the scapula or shoulder blade of the patient during the measurement procedures. This stability allows accurate measurement of the scapular position in three-dimensions, which is one unique feature of the device as compared to existing clinical products or non-research devices which are uni-dimensional measurement devices. For example, many one-dimensional measurement devices such as digital inclinometers, only measure one rotation at a time and always in line with gravity. As such, they can underestimate the intended motion being measured and are fully incapable of measuring motion occurring primary perpendicular to gravity (such as scapular internal rotation).

Figure 1C:
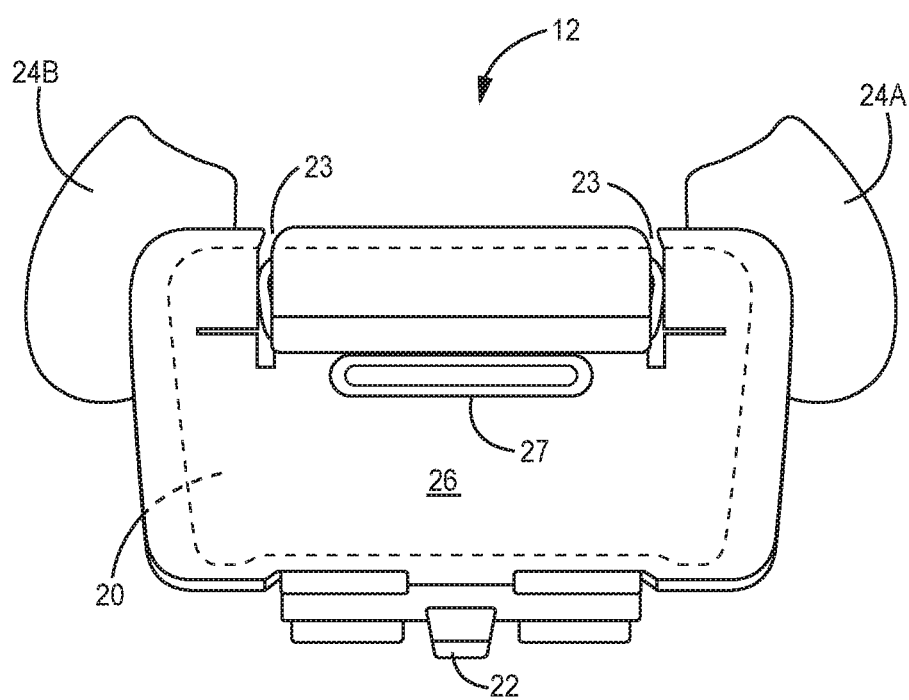
FIG. 1C is a diagram illustrating a backside view of another example of the mounting device of the 3D shoulder motion measurement system illustrated in FIG. 1A.

FIG. 1C is a diagram illustrating a backside view of another example of the mounting device 12 of the 3D shoulder motion measurement system 10 illustrated in FIG. 1A. As shown in FIG. 1C, the backside of mounting device 12 includes a back surface 26 that is a substantially planar surface across the central portions of the surface, and forms an exterior surface of mounting device 12 that is opposite and substantially parallel to one or more corresponding surfaces that form receptacle 20. The material forming mounting device 12 that is provided between the receptacle 20 and the back surface 26 provides a layer of material having a thickness and that provides the bottom, and in some examples the sides, for the receptacle 20, in a manner similar to that described above with respect to FIG. 1B. Instead of protrusions 25 on the back surface 26 as illustrated and described above with respect to FIG. 1B, the mounting device 12 as illustrated in FIG. 1C includes a raised ridge 27 extending outward from the back surface 26 of mounting device 12. In various examples, raised ridge 27 is positioned on the back surface 26 of mounting device 12, and is dimensioned with respect to a length, width, and a height such that ridge 27 extends above back surface 26 in order to provide the stabilizing function described above during a shoulder motion measurement procedure.

Figure 1D:
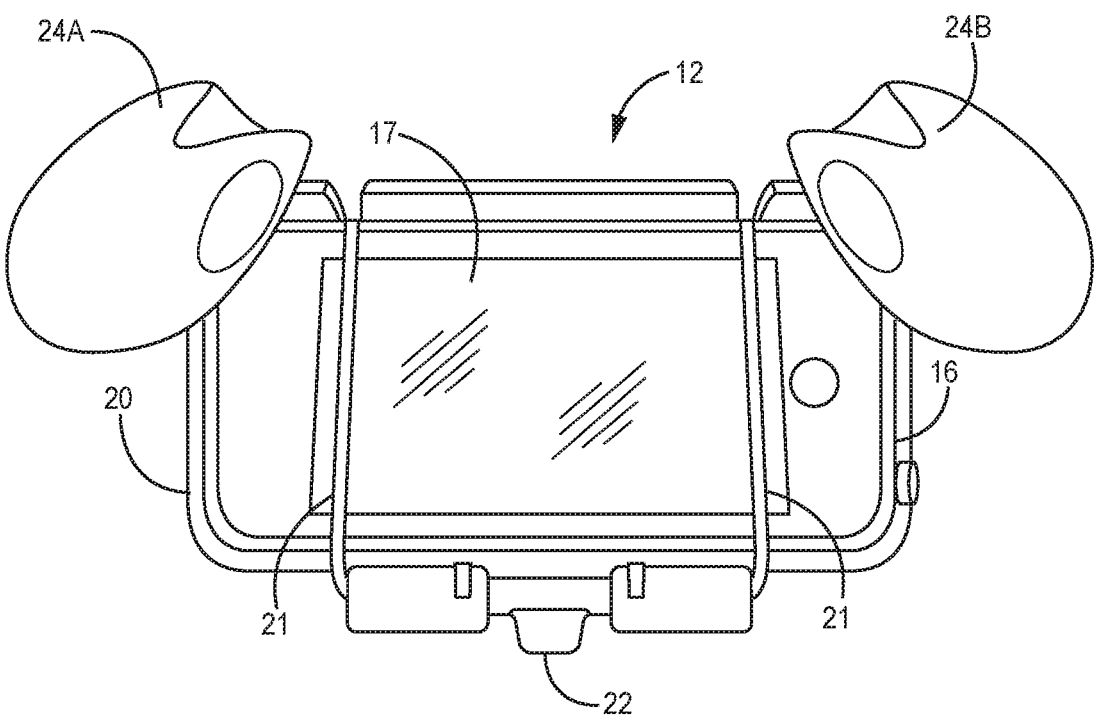
FIG. 1D is a diagram illustrating a front view of an exemplary shoulder motion measurement system when an electronic device has been inserted and secured at least partially within a receptacle of a mounting device.

FIG. 1D is a diagram illustrating a front view of an exemplary shoulder motion measurement system 10 when electronic device 16 has been received and secured at least partially within receptacle 20 of mounting device 12. As shown in FIG. 1D, electronic device 16 is secured via bands 21 in a manner that allows the display 17 of the electronic device to be viewed from the front side of system 10.

Figure 1E:
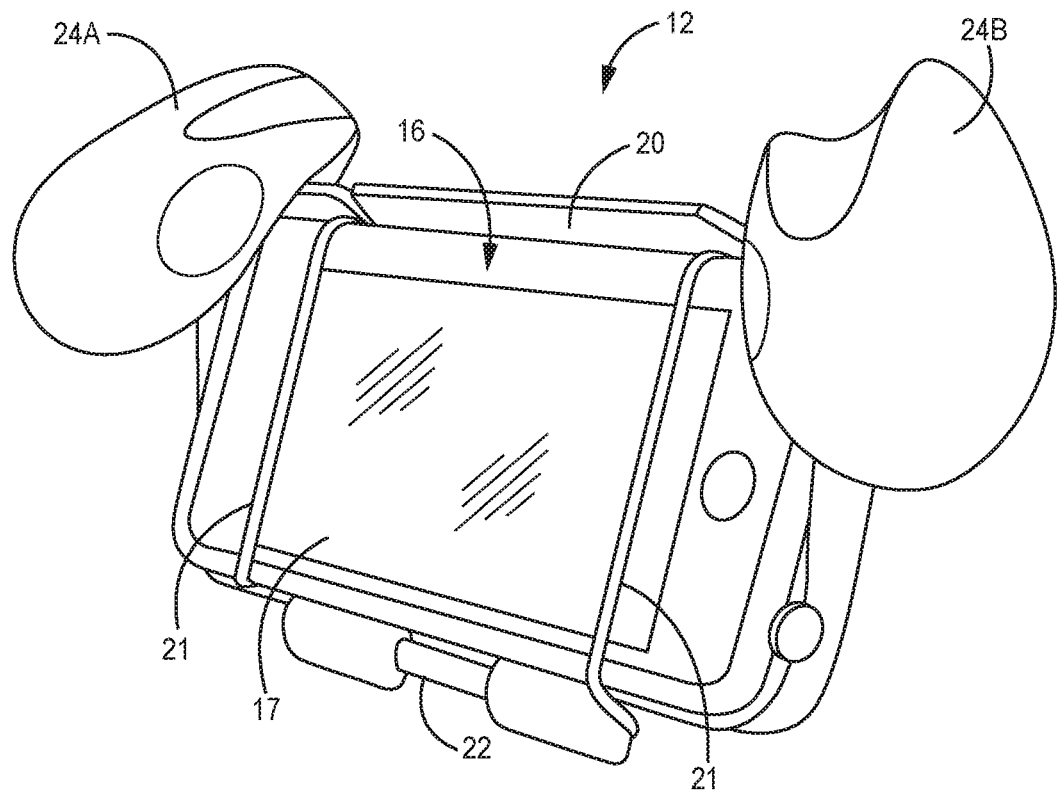
FIG. 1E is a diagram illustrating a perspective view of an exemplary shoulder motion measurement system when an electronic device has been inserted and secured at least partially within a receptacle of a mounting device.

FIG. 1E is a diagram illustrating a perspective view of an exemplary shoulder motion measurement system 10 when electronic device 16 has been received and secured at least partially within receptacle 20 of mounting device 12. As shown in FIG. 1E, electronic device 16 is secured via bands 21 in a manner that allows the display 17 of the electronic device to be viewed from the front side of system 10.

Figure 2A:
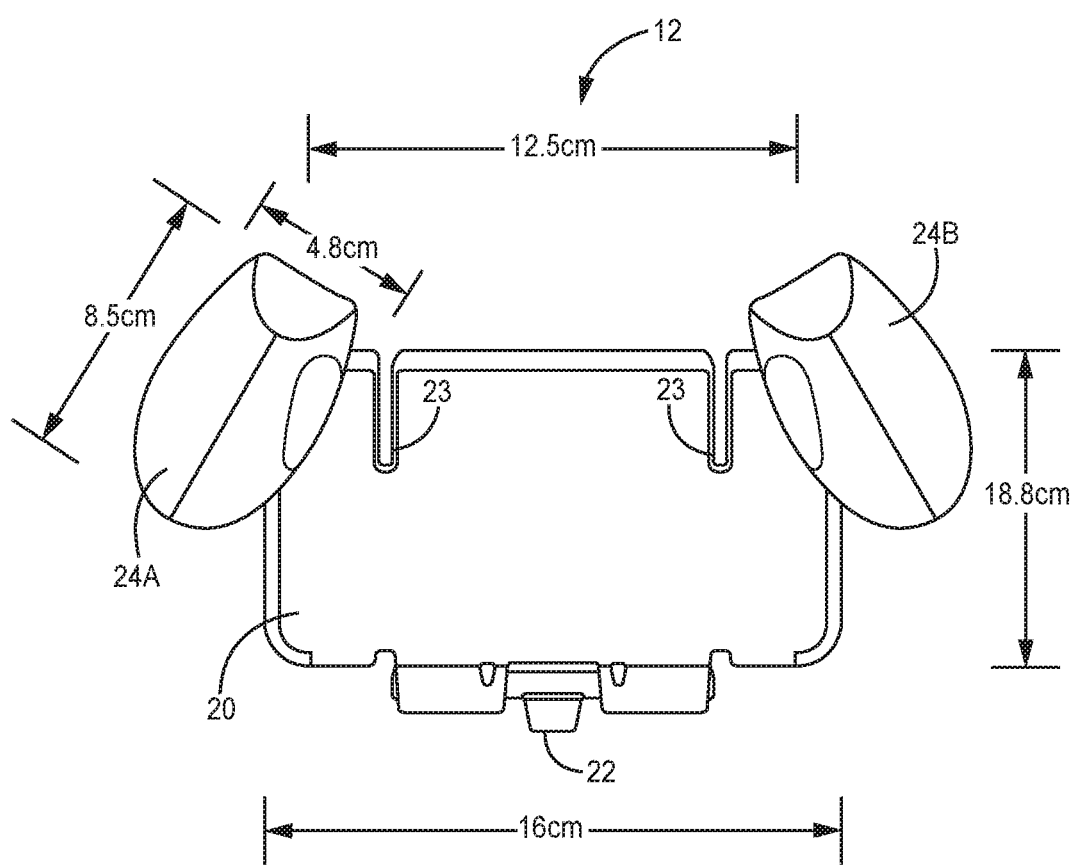
FIG. 2A is a diagram illustrating a front view of an example of a mounting device, including a receptacle and grips, in accordance with various techniques described in this disclosure.

FIG. 2A is a diagram illustrating a front view of an example of a mounting device 12, including receptacle 20 and grips 24A-24B, but less bands 21, in accordance with various techniques described in this disclosure. FIG. 2A includes illustration of some example dimensions associated with one example of mounting device 12. The values for the dimensions illustrated in FIG. 2A are provided as a non-limiting example of possible dimensions for the mounting device, wherein one or more different values for one or more of the illustrated dimensions as shown in FIG. 2A are contemplated for use in different examples of mounting device 12.

Figure 2B:
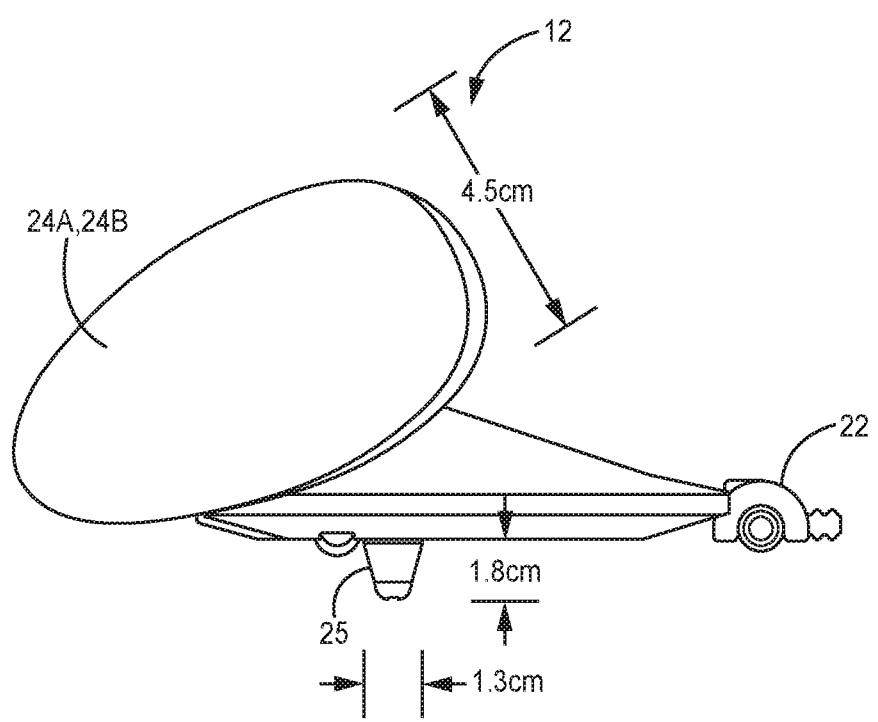
FIG. 2B is a diagram illustrating a profile view of the mounting device of FIG. 2A, including the receptacle, grips, and protrusions, in accordance with various techniques described in this disclosure.

FIG. 2B is a diagram illustrating a profile view of mounting device 12, including receptacle 20 and grips 24A-24B, protrusions 25, but less bands 21, of FIG. 2A. FIG. 2B includes illustration of some additional example dimensions associated with one example of mounting device 12. The values for the dimensions illustrated in FIG. 2B are provided as a non-limiting example of possible dimensions for the mounting device, wherein one or more different values for one or more of the illustrated dimensions as shown in FIG. 2B are contemplated for use in different examples of mounting device 12.

Figure 2C:
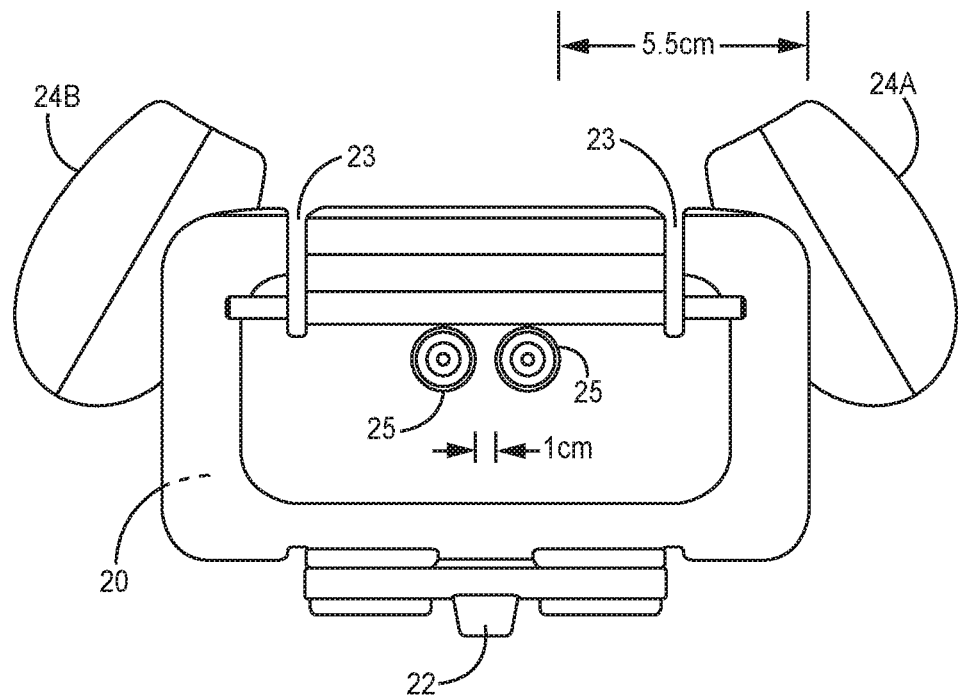
FIG. 2C is a diagram illustrating a backside view of the mounting device of FIG. 2A, including the receptacle, the grips, and the protrusions, in accordance with various techniques described in this disclosure.

FIG. 2C is a diagram illustrating a backside view of mounting device 12, including receptacle 20 and grips 24A-24B, protrusions 25, but less bands 21 of FIG. 2A. FIG. 2C includes illustration of some additional example dimensions associated with protrusions 25 for one example of mounting device 12. The values for the dimensions illustrated in FIG. 2C are provided as a non-limiting example of possible dimensions for the mounting device, wherein one or more different values for one or more of the illustrated dimensions as shown in FIG. 2C are contemplated for use in different examples of mounting device 12.

Figure 2D:
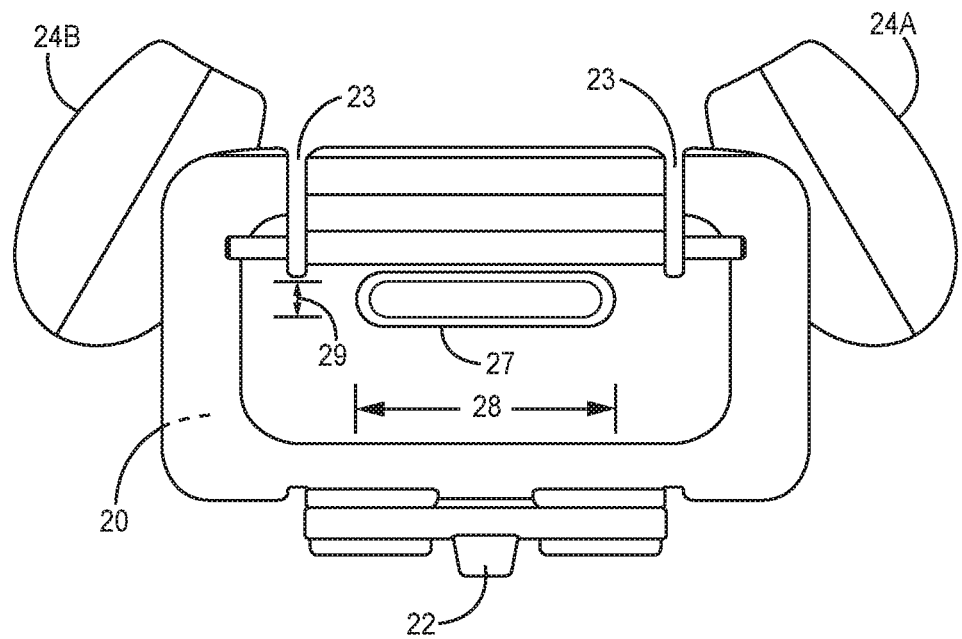
FIG. 2D is a diagram illustrating a profile view of the mounting device of FIG. 2A, including the receptacle, the grips, and a ridge, in accordance with various techniques described in this disclosure.

FIG. 2D is a diagram illustrating a profile view of mounting device 12, including receptacle 20 and grips 24A-24B, and ridge 27, but less bands 21, of FIG. 2A. FIG. 2D includes illustration of some additional example dimensions associated with ridge 27 for one example of mounting device 12. In some examples, a value for the length of ridge 27, as indicated by dimension 28, may be in a range of 2.5 to 4.5 cm. In some examples, a value for the width dimension of ridge 27, as indicated by dimension 29, may be in a range of 1.0 to 1.5 cm. The values for the dimensions illustrated in FIG. 2D are provided as a non-limiting example of possible dimensions for the mounting device, wherein one or more different values for one or more of the illustrated dimensions as shown in FIG. 2D are contemplated for use in different examples of mounting device 12.

FIG. 3 is a diagram 40 illustrating an example measurement system 10 aligned to the scapula of a patient 41 in accordance with various techniques described in this disclosure. As shown in FIG. 3, a user (not completely visible in FIG. 3) has his/her right hand 42 positioned on a first grip and his/her left hand 43 positioned of a second grip of the mounting device 12. System 10 includes an electronic device 16 positioned on and secured to mounting device 12, and configured to provide any of the features and functions described throughout this disclosure related to a three-dimensional (3D) shoulder motion measurement system.

As shown in FIG. 3, the user has positioned the mounting device 12 against the back of patient 41 and in the area of the patient's right scapula. The index finger on the right hand 42 of the user extends over the first grip to engage the patient's back in an area of the back adjacent to the first grip of the mounting device, and the index finger of the left hand 43 of the user extends over the second grip to engage the patient's back in an area of the back adjacent to the second grip. The user may manipulate the position of the index finger of the right hand 42, and thus the position of the first grip, to a location that corresponds with the posterior lateral acromion of the patient's right scapula. The user may also manipulate the position of the index finger of the left hand 43, and thus the position of the second grip, to a location that corresponds for example with the root of the spine of the patient's right scapula. Once the user has determined that the mounting device 12 is in the desired position, the user may actuate the electronic device 16, for example by tapping an area of the display screen or a button located on the electronic device, or using a voice command, to trigger the electronic device to take measurements. In various examples, triggering the electronic device 16 to take measurements may result in the display 17 displaying various information, including information associated with the shoulder measurements taken at the time the electronic device was triggered, as described in further detail below.

As shown in FIG. 3, once the mounting device 12 is positioned at the desired location relative to patient 41, the system may be triggered to take measurements with the patient's right arm in a particular first location, such as at rest near the side of the patient. Upon triggering the system 10 to take the measurement with the patient's arm at the first location, the user may determine that addition measurements may need to be taken with the patient's arm in the same position as shown in FIG. 3. The user may also instruct the patient to position their right arm in a different position, such as at some angle relative to the patient's side, and additional measurements may be taken with the patient's right arm positioned at these alternative positions, as further described throughout this disclosure.

At each position of the patient's arm, the user may trigger system 10 to take one or more sets of measurements related to the patient's scapula, as determined for examples example by sensor outputs provided by one or more sensors located within electronic device 16. The sensors may be controlled and/or triggered by the motion measurement application(s) downloaded to electronic device 16, and/or by software, firmware, and/or hardware provided by the electronic device prior to the downloading of the motion measurement applications. Processing of the signals received from the sensors may be performed, in whole or in part, by the one or more processors within electronic device 16, and running the one or more motion measurement applications downloaded to the electronic device to produce data related to the shoulder measurements taken with respect to patient 41. This data may be stored in the memory included within electronic device 16, and may be further processed to provide any of the displays and/or to generated generate any of the data related to patient 41 and/or other patients, as described throughout this disclosure, and any equivalents thereof.

These same positioning features and measurements may be provided and performed with respect to the patient's left scapula by having the user position the mounting device 12 at the desired location(s) along the patient's back adjacent to the patient's left scapula. As described in further detail below, electronic device 16 in various examples allows the user to provide inputs to the electronic device that indicate the area (e.g., left scapula, right scapula) where the system is being positioned at the time the system is triggered to take measurements. As also described in further detail below, electronic device 16 in various examples allows the user to provide inputs to the electronic device that indicate the arm position (e.g., relaxed at patient's side, flexed 90 degrees in sagittal plane, flexed to limit in sagittal plane), corresponding to the arm position of the patient at that time the system was trigger to take measurements.

Figure 4A:
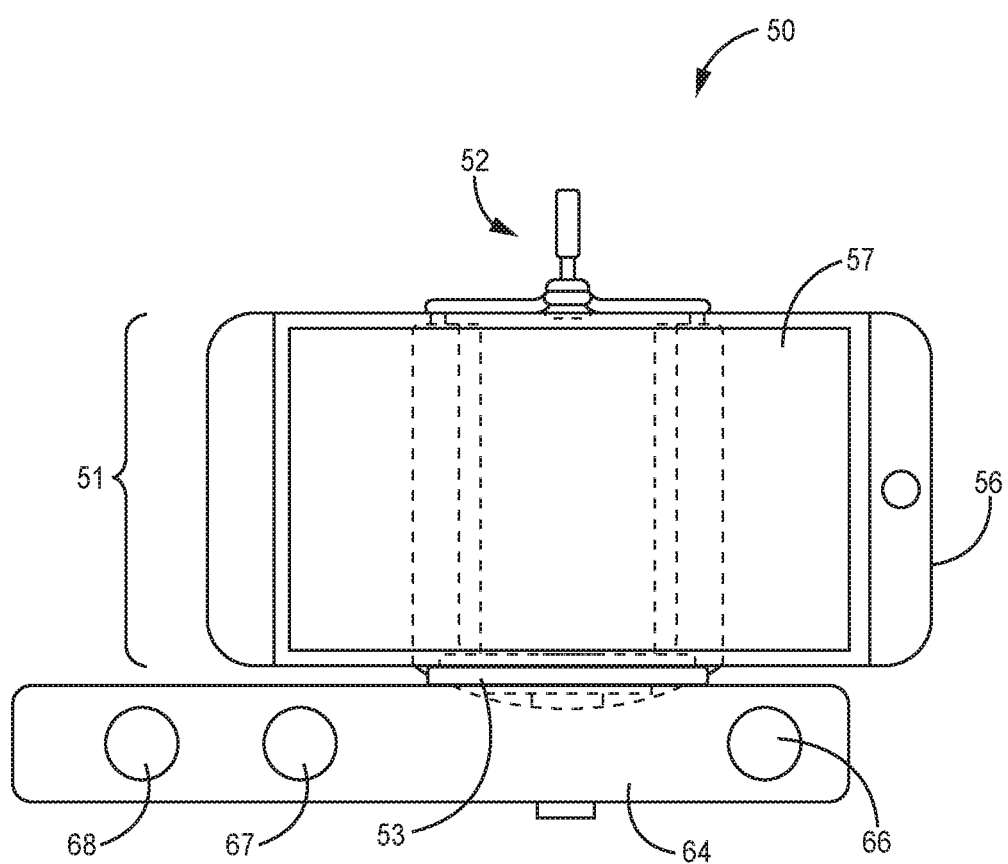
FIG. 4A illustrates a diagram of an example of a 3D shoulder motion measurement system in accordance with various techniques described in this disclosure.

FIG. 4A illustrates a diagram of an example of a 3D shoulder motion measurement system 50 in accordance with various techniques described in this disclosure. Shoulder motion measurement system 50 includes a mounting device 52 and an electronic device 56, as a mobile device such as a smartphone, secured in a fixed position relative to the mounting device 52. In various examples, electronic device 56 may be any of the examples of electronic device 16 and/or electronic device 120 illustrated and described throughout this disclosure, and may have one or more motion measurement applications downloaded to electronic device 56 to enable electronic device 56 to perform any of the measurements procedures and to provide any of the functions described throughout this disclosure with respect to electronic devices 16 and 120, and any equivalents thereof.

Mounting device 52 includes a receptacle area 51 that is sized and shaped to receive electronic device 56, and to secure electronic device 56 in a fixed orientation and position relative to a frame of reference of the mounting device. Once inserted, clamp 53 operates to engage and retain electronic device 56 within receptacle area 51. Mounting device 52 further includes a support member 64 having a set of spaced openings 66, 67, 68, that allow a user to extend his or her fingers for directly engaging the anatomical reference points necessary to measure scapula position of the patient during the diagnostic procedure.

Electronic device 56 may include one or more input/output devices, wherein a display 57 may provide a graphical display of the screens associated with calibration and/or measurements, and other data, such as patient data, collected as part of the processes described throughout this disclosure, and any equivalents thereof. Further, display 57 may by arranged to provide one or more selectable inputs, such as a graphical button, or a selectable input portion of the display screen, provided as a user-selectable input that when actuated, allows a user to provide inputs to the electronic device 56. Inputs may include an input indicating that the user wishes to have the electronic device 56 take measurements at the time the user input is received. In other examples, an input from a user, provided when a calibration screen is present on the display, may be received and processed by electronic device 56 as an indication that the user wishes to have the electronic device 56 perform a calibration procedure based on the current position of system 50. A user input to electronic device 56 may be provided by display 57, and when actuated provides as an indication to electronic device 56 that a user would like electronic device 56 to transmit data to one or more external devices (not shown in FIG. 4A, but for example external devices 29 shown in FIG. 1A). The request for information may include a request for other data, for example other patient data, that is stored in a memory of electronic device 56.

Figure 4B:
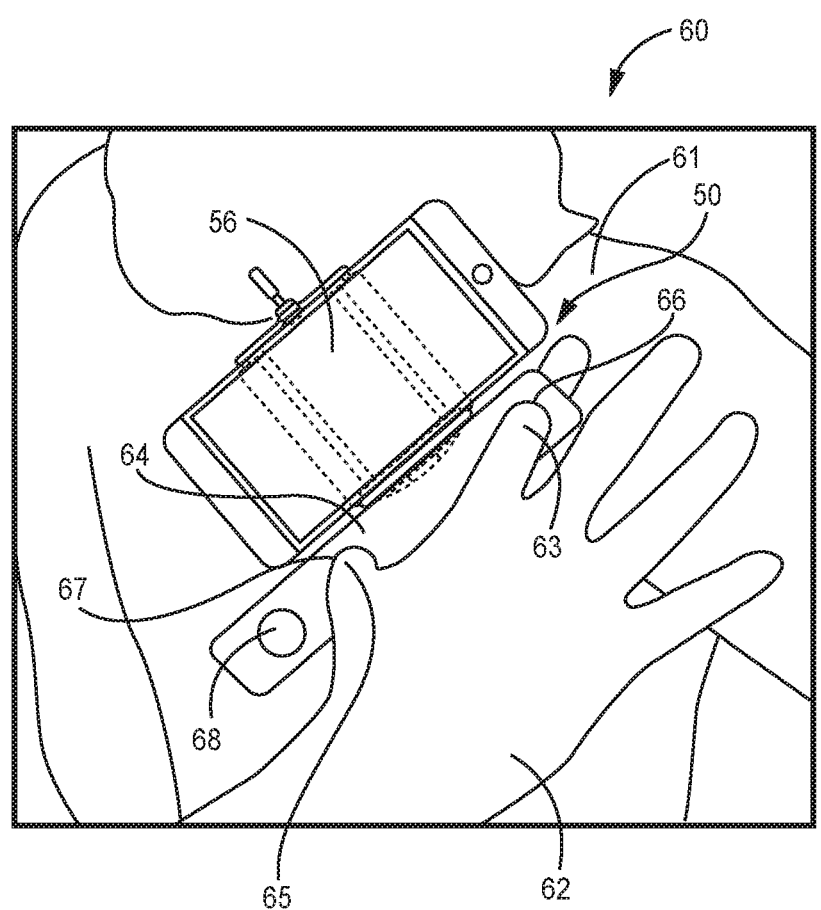
FIG. 4B illustrates a diagram of an example diagnostic procedure using the shoulder motion measurement system of FIG. 4B in accordance with various techniques described throughout this disclosure.

FIG. 4B illustrates a diagram 60 of an example diagnostic procedure using shoulder motion measurement system 50 in accordance with various techniques described throughout this disclosure. In this example, a user 62 (not fully shown in FIG. 4B) places the user's index finger 63 through opening 66 of support member 64, and places the user's thumb 65 through opening 67 of support member 64. The positioning of the user's finger and thumb allows the user to palpate the anatomic reference points on the scapula of patient 61. The spacing and arrangement of the openings 66, 67, and 68 are designed in such a manner as to allow hands of various sizes to comfortably and securely locate the necessary anatomic reference points on a variety of scapula sizes. Having direct finger contact with the landmarks improves accuracy through proprioceptive feedback. In addition, spacing of the device may be based on a set of average anatomical spacing of landmarks, as well as typical variation across individuals.

Once the user has positioned system 50 in a desired position and orientation relative to the scapula of patient 61, the user may actuate an input on electronic device 56 as described above, to indicate to the electronic device 56 that system 50 is in a desired position, and that the system is to proceed with taking shoulder motion measurements.

Figure 4C:
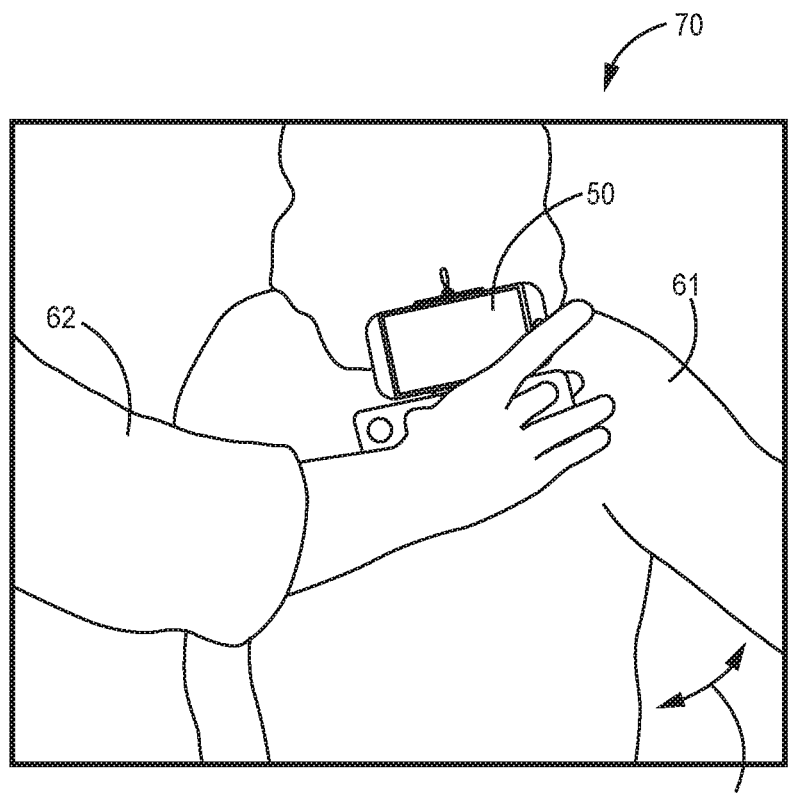
FIGS. 4C-4D illustrate diagrams of additional examples of diagnostic procedures using the shoulder motion measurement system of FIG. 4A in accordance with various techniques described throughout this disclosure.
Figure 4D:
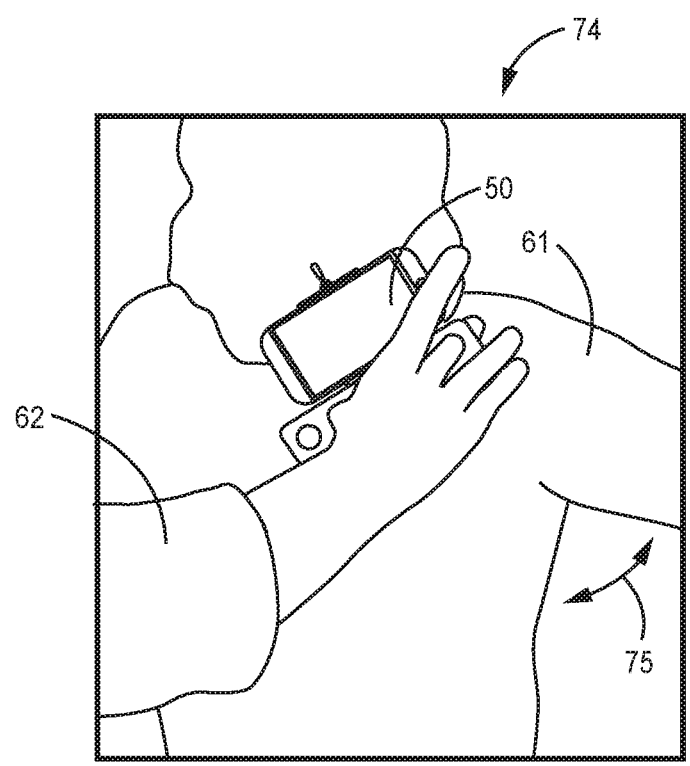

FIGS. 4C and 4D illustrate diagrams 70, 74 of additional examples of diagnostic procedures using shoulder motion measurement system 50 in accordance with various techniques described throughout this disclosure. In the example shown in diagram 70 in FIG. 4C, a user 62 (not fully shown in FIG. 4C) has placed the user's index finger and thumb through openings in support member 64 of system 50, and has positioned system 50 on the scapula of patient 61, in a manner similar to that illustrated and described above with respect to FIG. 4B. Again, the positioning of the user's finger and thumb allows the user to palpate the anatomic reference points on the scapula of patient 61.

As shown in diagram 70, the right arm of patient 61 is positioned to form an angle 73 relative to the patient's right arm and the right side of the patient. In various examples, the angle 73 may be an arm position for which the user wishes to take shoulder motion measurements for patient 61. As such, when system 50 and patient 61 are all positioned as shown in diagram 70, the user 62 may provide an input to system 50, triggering system 50 to take shoulder measurements. These measurements may then be taken, processed, stored in a memory, may be displayed by system 50, and/or communicated to one or more external devices (not shown in FIG. 4C) based on receiving the input actuation from user 62. In various examples, system 50 may also allow user 62 to input information into electronic device of system 50 associated with a value for angle 73 and/or the patient's arm position at the time the measurements were taken. The input of this information may take place either before or after system 50 performed the shoulder motion measurements associated with the positions of the system 50 and patient 61 as illustrated in FIG. 4C.

In the example shown in diagram 74 in FIG. 4D, a user 62 (not fully shown in FIG. 4D) has places the user's index finger and thumb through openings in support member 64 of system 50, and has positioned system 50 on the scapula of patient 61, in a manner similar to that illustrated and described above with respect to FIG. 4B. Again, the positioning of the user's finger and thumb allows the user to palpate the anatomic reference points on the scapula of patient 61. However, an angle 75 associated with the angle between the patient's right arm and the patient's right side has increased in value relative to the value of angle 73 illustrated in diagram 70.

In various examples, once patient 61 has positioned the patient's right arm to the position represented as angle 75, and the user has positioned system 50 as also illustrated in diagram 74, the user may determine that this is another arrangement for which the user wishes to take shoulder motion measurements for patient 61. As such, when system 50 and patient 61 are all positioned as shown in diagram 74, the user 62 may provide an input to system 50, triggering system 50 to take shoulder measurements. These measurements may then be taken, processed, stored in a memory, displayed by system 50, and/or communicated to one or more external devices (not shown in FIG. 4D) based on receiving the input actuation from user 62. In various examples, system 50 may also allow user 62 to input information into electronic device of system 50 associated with a value for angle 75 and/or the patient's arm position at the time the measurements were taken. The input of this information may take place either before or after system 50 performs the shoulder motion measurements associated with the positions of the system 50 and patient 61 as illustrated in FIG. 4D. In addition, any and/or all measurements taken with respect to patient 61, both taken at one time, e.g., taken on a same day, or for example at different times, e.g., taken at different times over a period of days, weeks, months, or years, may all be associated with one another by the application(s) running on the electronic device of system 50, for example using a client identification number, as further described below. In various examples, the data associated with measurements taken with respect to patient 61 as shown in diagrams 70 and 74 may also be uploaded from system 50 to one or more external devices (not shown in FIGS. 4C-4D, but for example external devices 29 shown and described with respect to FIG. 1A), and/or downloaded to system 50 from these external devices, in order to further concatenate, compare, and/or combine this data with data collected and/or generated at some time that corresponds to patient 61, and/or other patients.

Figure 5A:
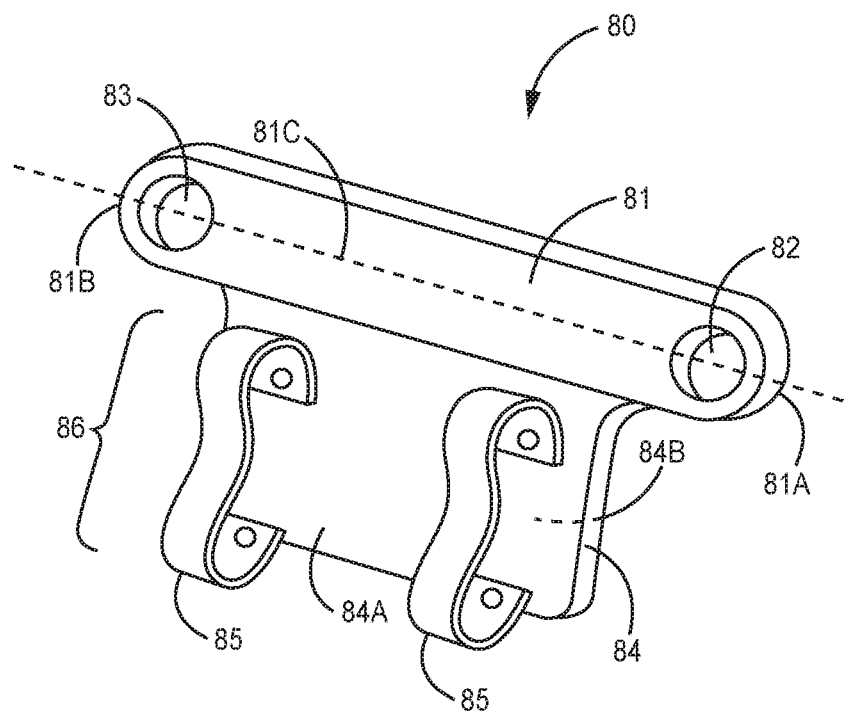
FIGS. 5A-5B are diagrams illustrating an example of a mounting device for use in a 3D shoulder motion measurement system in accordance with various techniques described in this disclosure.
Figure 5B:
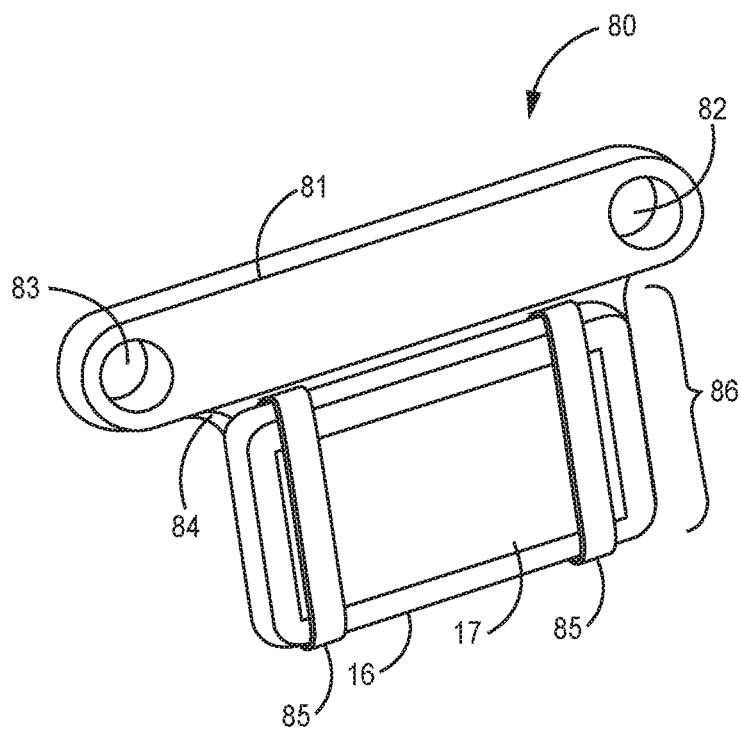

FIGS. 5A-5B are diagrams illustrating an example of a mounting device 80 for use in a 3D shoulder motion measurement system in accordance with various techniques described in this disclosure. As shown in FIG. 5A, mounting device 80 includes a support member 81 comprising an elongated shaped material having a longitudinal axis 81C, and including a first opening 82 that passed through the support member 81 near a first end 81A of the support member, and a second opening 83 that passes through the support member 81 near a second end 81B opposite the first end 81A. In various examples, support member 81 may be formed of a molded material, such as a polymeric material, for example nylon or polyurethane, or polycarbonate, that has been formed generally into the elongated shape illustrated in FIG. 5A.

Support member 81 is coupled along a portion of a bottom edge of the support member to a backing plate 84. In various examples, backing plate 84 is a flat sheet of material having generally a rectangular shape, a front surface 84A, and a back surface 84B. Backing plate 84 may be formed of a molded material, such as a polymeric material, and may be a same or a different material used to form support member 81. Backing plate 84 may be formed of a material, such as a polymeric, that is generally rigid enough to maintain the backing plate in the flat shape and in the orientation relative to support member 81 as illustrated in FIG. 5A when unsupported by any external structures other than support member 81. In various examples, backing plate 84 is a flexible material, such as a natural or artificial elastomer material, that is flexibly coupled to the support member 81. In various examples, backing plate 84 is coupled to the support member 81 along one of the sides of the backing plate 84. Backing plate 84 may be coupled to support member 81 so that backing plate 84 extends in a plane that is coplanar with or in a plane that is parallel with a backside surface of the support member 81.

As shown in FIG. 5A, backing plate 84 includes a pair of mounting straps 85, each mounting strap coupled to the backing plate in a first and a second position along a dimension of the front surface 84A of the backing plate 84 so that each mounting strap 85 is oriented in a direction that is perpendicular to the longitudinal axis 81C of the support member 81. Mounting straps 85 may be formed of a polymeric and elastic material, such as an elastomer, for example natural or synthetic rubber or silicone. In various examples, mounting straps 85 may be formed of a fabric woven with an elastic material to form resiliently expandable straps. Mounting straps are arranged to be resiliently expanded or stretched to receive and then to secure an electronic device (such as electronic device 16 as shown and described with respect to FIG. 1A-1D), in a receptacle area 86 of mounting device 80 as illustrated for example in FIG. 5B.

The dimensions of mounting device 80, and in particular the spacing of openings 82 and 83 along the longitudinal axis of support member 81, may be arranged to provide any combination of the features and functions described throughout this disclosure related to mounting and securing an electronic device in the receptacle area 86. For example, the spacing between opening 82 and 83 along the longitudinal axis of support member 81 may have a value that allows a user (not shown in FIG. 5A) to insert a first finger into opening 82 and a thumb into opening 83 in order to position mounting device 80 against a patient as part of a measurement procedure, in a similar manner as illustrated for example in FIG. 3. In other examples, a user may insert a first finger from one of the user's hands into opening 82, and a second finger from the user's other hand into opening 83 in order to position mounting device 80 against a patient as part of a measurement procedure. In various examples, the dimensions of backing plate 84 and the location, arrangement, and orientation of mounting straps 85 are such that receptacle area 86 is configured to accept a range of sizes of electronic devices, including a range of sizes of devices such as smartphones, personal digital assistant (PDA), or other electronic devices that may be programmed and used as part of a 3D shoulder measurement system as described herein and any equivalents thereof.

As shown in FIG. 5B, mounting device 80 is illustrated as having received and secured the electronic device 16 in the receptacle area 86 to provide a 3D shoulder motion measurement system. The 3D shoulder motion measurement system as illustrated in FIG. 5B may be arranged to allow a user (not shown in FIG. 5B), to engage openings 82 and 83 for the purpose of positioning mounting device 80 and electronic device 16 in a desired position on a patient for the purpose of taking measurement according to any of the techniques described throughout this disclosure, and any equivalents thereof. Further, mounting straps 85 are configured to maintain the electronic device 16 in a fixed position relative to support member 81 once the electronic device has been received and secured using mounting straps 85 in receptacle area 86 during the movements of the mounting device that would be incurred as part of any calibration and measurement procedures that the measurement system as illustrated in FIG. 5B would be designed to perform, including preventing electronic device 16 from sliding out of the receptacle area 86 when the mounting device 80 is tilted at various angles relative to gravity during these calibration and/or measurement procedures.

In addition, when electronic device 16 is secured in receptacle area 86, the arrangement of support member 81, backing plate 84, and mounting straps 85 for example as illustrated in FIG. 5B allow a user (not shown in FIG. 5B) visual access to display 17 of electronic device 16. The arrangement as illustrated in FIG. 5B in various examples also allows the user to contact one or more portions of the display 17 to provide inputs to electronic device 16 as part of any of the calibration and/or measurement procedures described throughout this disclosure, and any equivalents thereof.

Figure 6A:
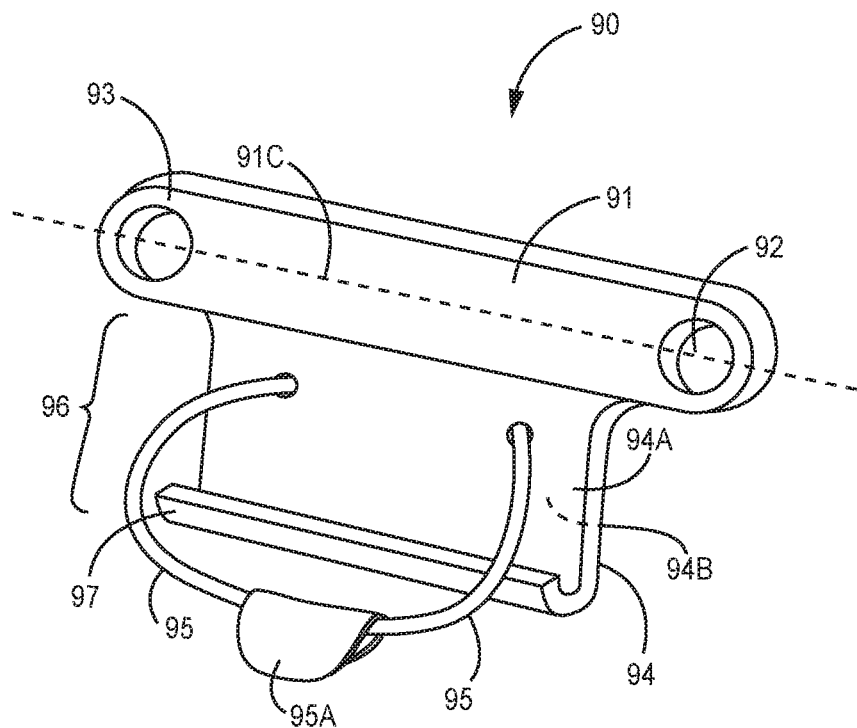
FIGS. 6A-6B are diagrams illustrating an example of a mounting device for use in a 3D shoulder motion measurement system in accordance with various techniques described in this disclosure.
Figure 6B:
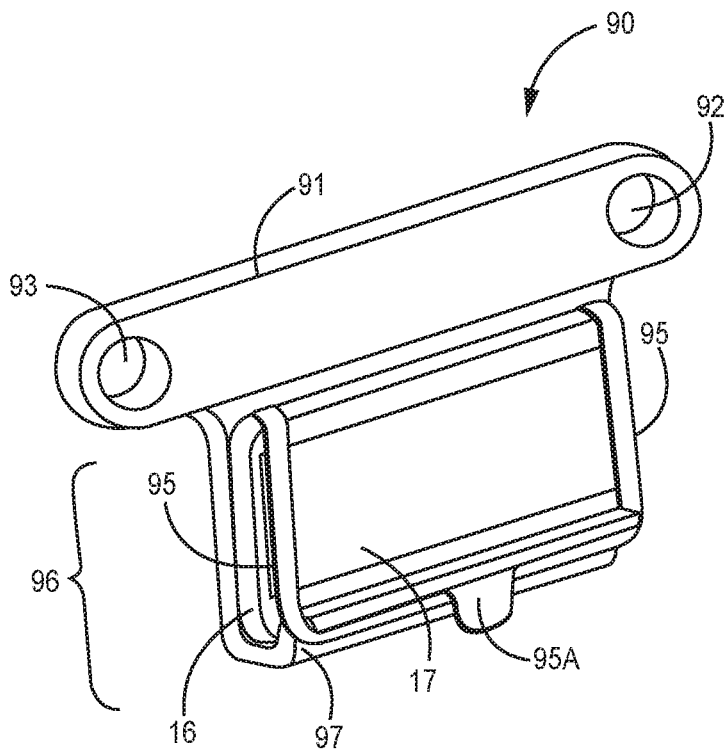

FIGS. 6A-6B are diagrams illustrating an example of a mounting device 90 for use in a 3D shoulder motion measurement system in accordance with various techniques described in this disclosure. As shown in FIG. 6A, mounting device 90 includes a support member 91 comprising an elongated shaped material having a longitudinal axis 91C, and including a first opening 92 that passes through the support member 91 near a first end 91A of the support member, and a second opening 93 that passes through the support member 91 near a second end 91B opposite the first end 91A. In various examples, support member 91 may be formed of a molded material, such as a polymeric material, for example nylon or polyurethane, or polycarbonate, that has been formed generally into the elongated shape illustrated in FIG. 6A.

Support member 91 is coupled along a portion of a bottom edge of the support member to a backing plate 94. In various examples, backing plate 94 is a flat sheet of material having generally a rectangular shape, a front surface 94A, a back surface 94B. Backing plate 94 may also include a retention lip 97 formed along a side of backing plate 94 opposite the side of backing plate 94 that is coupled to support member 91. Backing plate 94 and lip 97 may be formed of a molded material, such as a polymeric material, and may be a same or a different material used to form support member 91. Backing plate 94 and lip 97 may be formed of a material, such as a polymeric material, that is generally rigid enough to maintain the backing plate in the flat shape and the lip 97 in the orientation relative to each other and to support member 91 as illustrated in FIG. 5A when unsupported by any external structures other than support member 91. In various examples, backing plate 94 and/or lip 97 are formed from a flexible material, such as a natural or artificial elastomer material, that is flexibly coupled to the support member 91. In various examples, backing plate 94 is coupled to the support member 91 along one of the sides of the backing plate 94. Backing plate 94 may be coupled to support member 91 so that backing plate 94 extends in a plane that is coplanar with or in a plane that is parallel with a backside surface of the support member 91.

As shown in FIG. 6A, backing plate 94 includes a mounting strap 95, that is coupled to the backing plate 94 in a first and a second position within the front surface 94A of the backing plate. Mounting strap 95 may be formed of a polymeric and elastic material, such as an elastomer, for example natural or synthetic rubber or silicone. In various examples, mounting strap 95 may be formed of a fabric woven with an elastic material to form a resiliently expandable strap. Mounting strap 95 is arranged to be resiliently expanded or stretched to receive and then to secure an electronic device (such as electronic device 16 as shown and described with respect to FIG. 1A-1D), in a receptacle area 96 of mounting device 90, as illustrated for example in FIG. 6B. In various examples, mounting strap 95 includes a latch portion 95A coupled to mounting strap 95, and arranged so that latch portion 95A engages lip 97 when mounting strap 95 has been extended around an electronic device received in receptacle area 96 to secure mounting strap 95 to lip 97, and thus secure the electronic device in receptacle area 96.

The dimensions of mounting device 90, and in particular the spacing of openings 92 and 93 along the longitudinal axis of support member 91, may be arranged to provide any combination of the features and functions described throughout this disclosure related to mounting and securing electronic devices in the receptacle area 96. For example, the spacing between opening 92 and 93 along the longitudinal axis 91C of support member 91 may have a value that allows a user (not shown in FIG. 6A) to insert a first finger into opening 92 and a thumb into opening 93 in order to position mounting device 90 against a patient as part of a measurement procedure, in a similar manner as illustrated for example in FIG. 3. In other examples, a user may insert a first finger from one of the user's hands into opening 92, and a second finger from the user's other hand into opening 93 in order to position mounting device 90 against a patient as part of a measurement procedure. In various examples, the dimensions of backing plate 94 and the location, arrangement, and orientation of lip 97 and mounting strap 95 are such that receptacle area 96 is configured to accept a range of sizes of electronic devices, including a range of sizes of devices such as smartphones, personal digital assistants (PDAs), or other electronic devices that may be programmed and used as part of a 3D shoulder measurement system as described herein and any equivalents thereof.

As shown in FIG. 6B, mounting device 90 is illustrated as having received and secured the electronic device 16 in the receptacle area 96 to provide a 3D shoulder motion measurement system. The 3D shoulder motion measurement system as illustrated in FIG. 6B may be arranged to allow a user (not shown in FIG. 6B), to engage openings 92 and 93 for the purpose of positioning mounting device 90 and electronic device 16 in a desired position on a patient for the purpose of taking measurement according to any of the techniques described throughout this disclosure, and any equivalents thereof. Further, mounting strap 95 and lip 97 are configured to maintain the electronic device 16 in a fixed position relative to support member 91 once the electronic device has been received and secured using mounting strap 95 in receptacle area 96 during the movements of the mounting device that would be incurred as part of any calibration and measurement procedures that the measurement system as illustrated in FIG. 6B would be designed to perform, including preventing electronic device 16 from sliding out of the receptacle area 96 when the mounting device 90 is tilted at various angles relative to gravity during these calibration and/or measurement procedures. In addition, when electronic device 16 is secured in receptacle area 96, the arrangement of support member 91, backing plate 94 including lip 97, and mounting strap 95 for example as illustrated in FIG. 6B allow a user (not shown in FIG. 6B), visual access to display 17. The arrangement as illustrated in FIG. 6B in various examples also allows the user to contact one or more portions of the display 17 in order to provide inputs to electronic device 16 as part of any of the calibration and/or measurement procedures described throughout this disclosure, and any equivalents thereof.

Figure 7A:
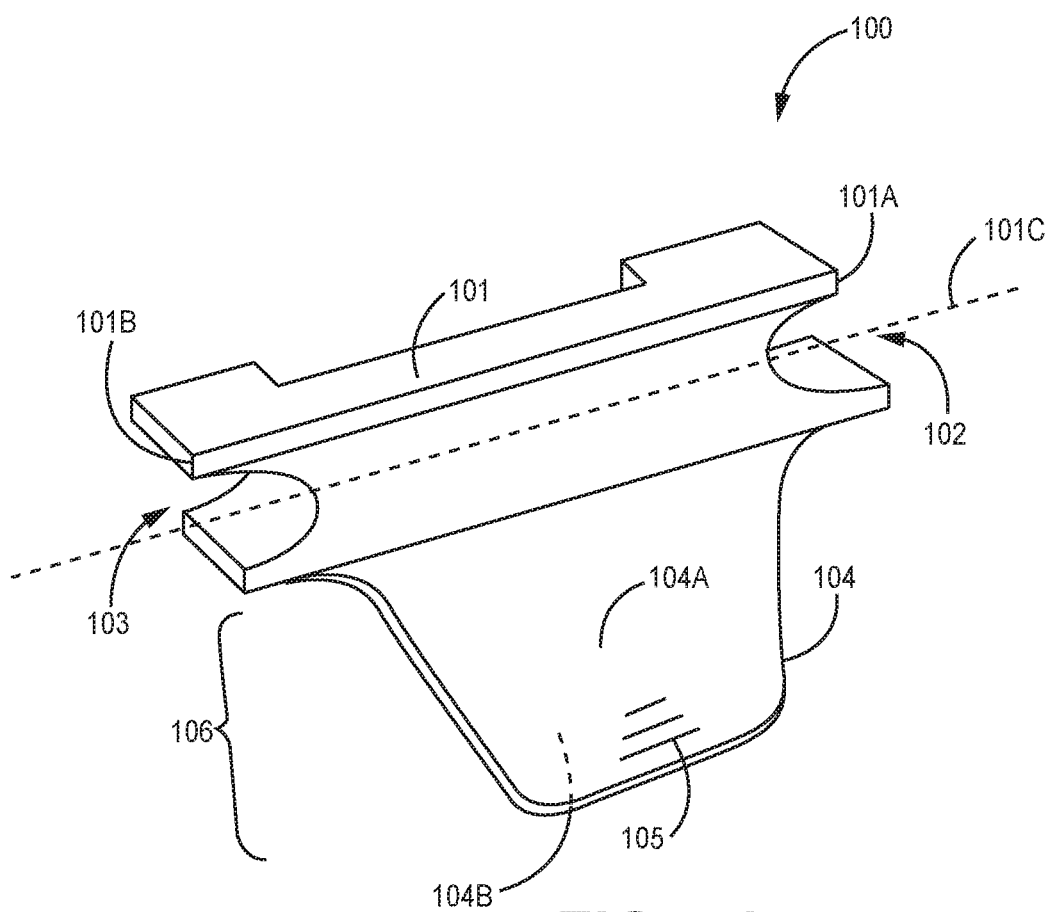
FIGS. 7A-7B are diagrams illustrating an example of a mounting device for use in a 3D shoulder motion measurement system in accordance with various techniques described in this disclosure.
Figure 7B:
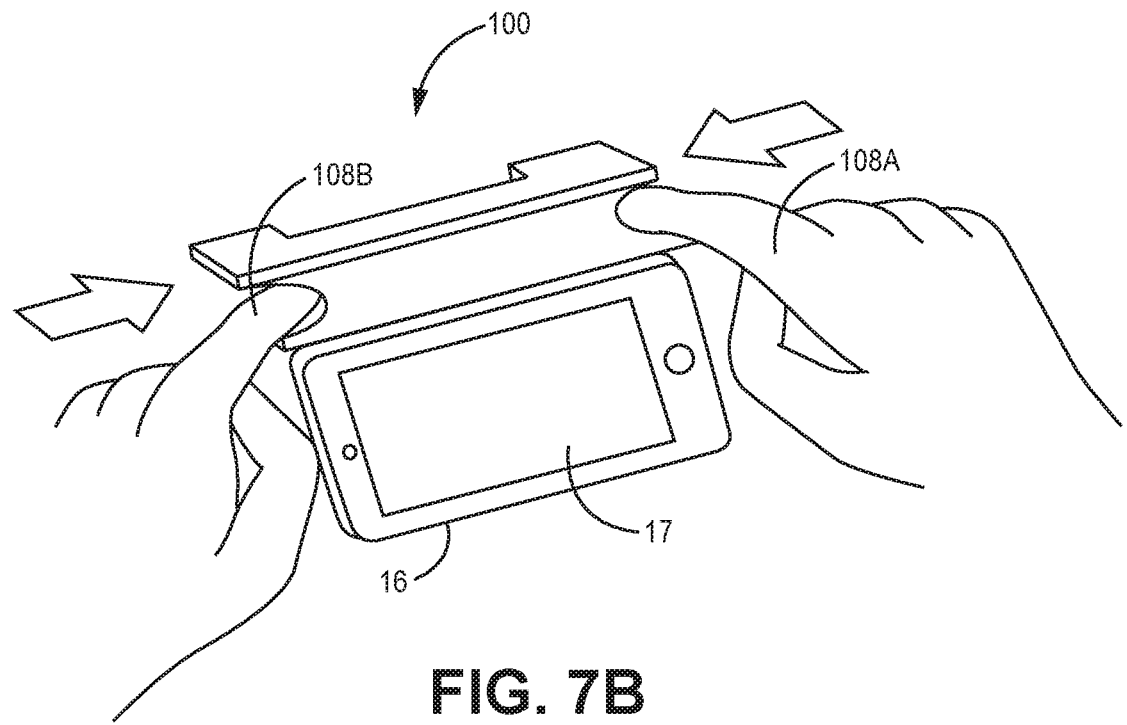

FIGS. 7A-7B are diagrams illustrating an example of a mounting device 100 for use in a 3D shoulder motion measurement system in accordance with various techniques described in this disclosure. As shown in FIG. 7A, mounting device 100 includes a support member 101 comprising an elongated shaped material having a longitudinal axis 101C, and including a first opening 102 that passes through the support member 101 and is open through to a first end 101A of the support member, and a second opening 103 that passes through the support member 91 and that is open through to a second end 101B opposite the first end 101A. In various examples, support member 101 may be formed of a molded material, such as a polymeric material, for example nylon or polyurethane, or polycarbonate, that has been formed generally into the elongated shape illustrated in FIG. 7A.

Support member 101 is coupled along a portion of a bottom edge of the support member to a backing plate 104. In various examples, backing plate 104 is a flat sheet of material having generally a rectangular shape or a tapered dimension along the side edges of backing plate 104 as the side edges extend away from support member 101. Backing plate 104 includes a front surface 104A, and a back surface 104B. Backing plate 104 may be formed of a molded material, such as a polymeric material, and may be a same or a different material used to form support member 101. Backing plate 104 may be formed of a material, such as a polymeric material, that is generally rigid enough to maintain the backing plate in the flat shape and in the orientation relative to support member 101 as illustrated in FIG. 7A when unsupported by any external structures other than support member 101. In various examples, backing plate 104 is a flexible material, such as a natural or artificial elastomer material, that is flexibly coupled to the support member 101. In various examples, backing plate 104 is coupled to the support member 101 along one of the sides of the backing plate 104. Backing plate 104 may be coupled to support member 101 so that backing plate 104 extends in a plane that is coplanar with or in a plane that is parallel with a backside surface of the support member 101.

As shown in FIG. 7A, backing plate 104 includes latch portion 105, formed as a portion of backing plate 104 near the edge of backing plate 104 opposite the edge of backing plate 104 that is coupled to support member 101. Latch portion 105 may be formed of a material that is releasably securable, such as a Velcro-like material that may securely hold an electronic device 16 or an off-the-shelf case for such a device to the backing plate 104. In some examples, an elastic component that wraps around the electronic device and/or the off-the-shelf case may be secured to, for example glued to backing plate 104, the elastic component arranged to releasably secure the electronic device to the backing plate 104. Latch portion 105 may include a material that allows a back surface of an electronic device 16 to come into contact with latch portion 105 so that electronic device 16 is releasable secured to the backing plate 104 in a receptacle area 106 of mounting device 100 as illustrated for example in FIG. 6B.

The dimensions of mounting device 100, and in particular the spacing of openings 102 and 103 along the longitudinal axis 101C of support member 101 may be arranged to provide any combination of the features and functions described throughout this disclosure related to mounting and securing electronic devices in the receptacle area 106. For example, the spacing between opening 102 and 103 along the longitudinal axis 101C of support member 101 may have a value that allows a user (not fully shown in FIG. 7A) to insert a first finger 108A into opening 102 and a thumb or a second finger 108B into opening 103 in order to position mounting device 90 against a patient as part of a measurement procedure, in a similar manner as illustrated for example in FIG. 3. In various examples, the dimensions of backing plate 104 and the location, arrangement, and orientation of backing plate 104 and latch portion 105 are such that receptacle area 106 is configured to accept a range of sizes of electronic devices, including a range of sizes of devices such as smartphones, personal digital assistant (PDA), or other electronic devices that may be programmed and used as part of a 3D shoulder measurement system as described herein and any equivalents thereof.

As shown in FIG. 7B, mounting device 100 is illustrated as having received and secured the electronic device 16 in the receptacle area 106 to provide a 3D shoulder motion measurement system. The 3D shoulder motion measurement system as illustrated in FIG. 7B may be arranged to allow a user (not fully shown in FIG. 7B), to engage openings 102 and 103 for the purpose of positioning mounting device 100 and electronic device 16 in a desired position on a patient for the purpose of taking measurement according to any of the techniques described throughout this disclosure, and any equivalents thereof. Further, backing plate 104 and latch portion 105 are configured to maintain the electronic device 16 in a fixed position relative to support member 101 once the electronic device has been received and secured in receptacle area 106 during the movements of the mounting device 100 that would be incurred as part of any calibration and measurement procedures that the measurement system as illustrated in FIG. 7B would be designed to perform, including preventing electronic device 16 from sliding out or away from the receptacle area 106 when the mounting device 100 is held up and/or tilted at various angles relative to gravity during these calibration and/or measurement procedures.

In addition, when electronic device 16 is secured in receptacle area 106, the arrangement of support member 101, backing plate 104, and latch portion 105 for example as illustrated in FIG. 7B allows a user (not fully shown in FIG. 7B) visual access to display 17 of electronic device 16. The arrangement as illustrated in FIG. 7B in various examples also allows the user to contact one or more portions of the display 17 in order to provide inputs to electronic device 16 as part of any of the calibration and/or measurement procedures described throughout this disclosure, and any equivalents thereof. In some examples, when electronic device 16 is secured in receptacle area 106 as shown in FIG. 7B, backing plate 104 and latch portion 105 are in contact with a back surface only, or a back surface and one side edge of the electronic device 16, and therefore allow full access, both visually and with respect to contacting display 17 of the electronic device.

Figure 8A:
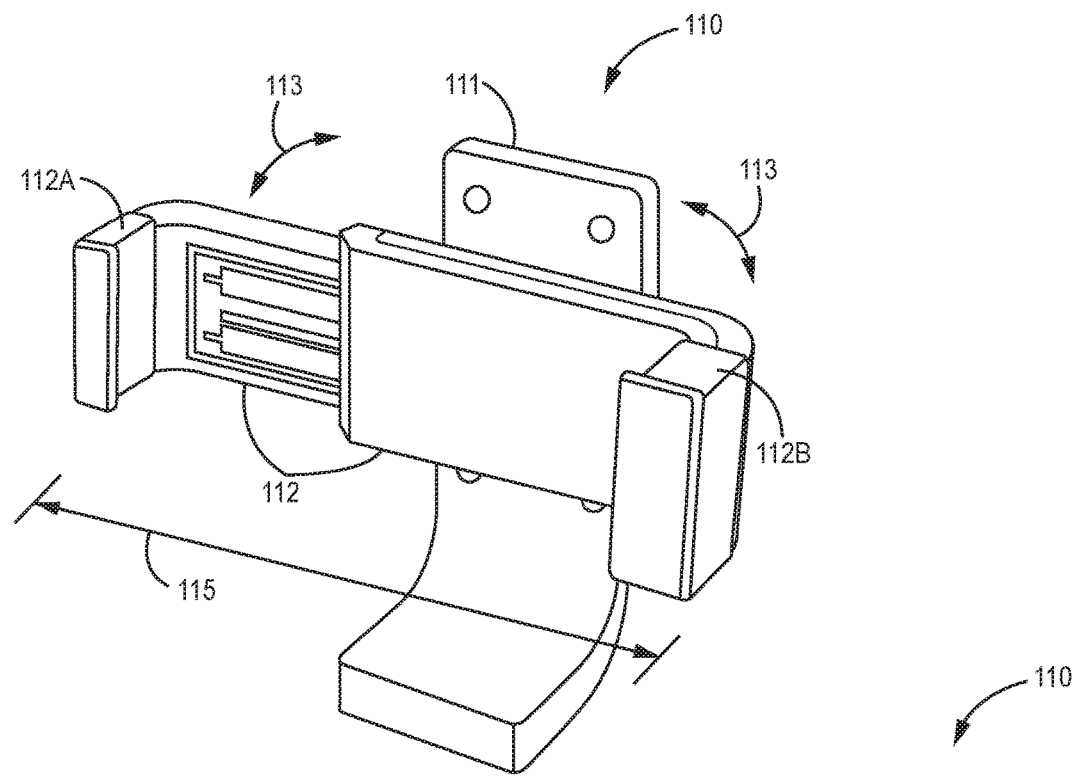
FIGS. 8A-8B are diagrams illustrating an example of a mounting device for use in a 3D shoulder motion measurement system in accordance with various techniques described in this disclosure.
Figure 8B:
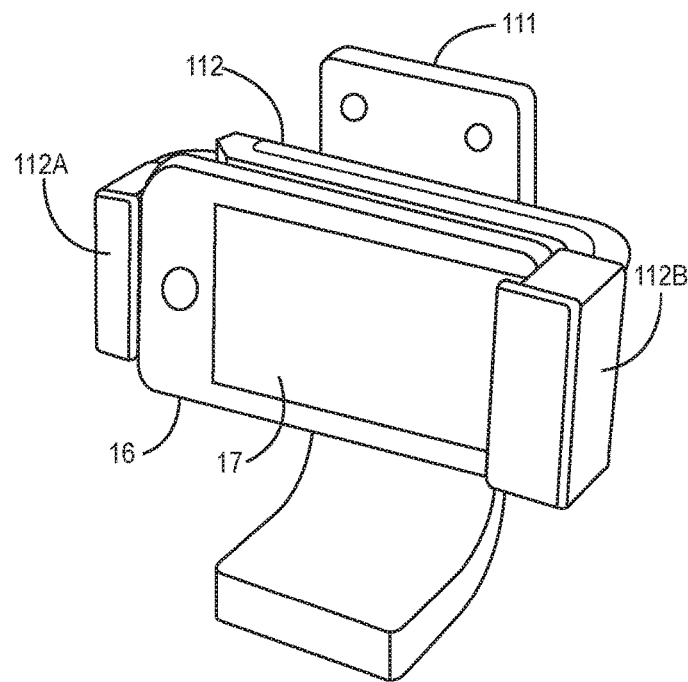

FIGS. 8A-8B are diagrams illustrating an example of a mounting device for use in a 3D shoulder motion measurement system in accordance with various techniques described in this disclosure. As shown in FIG. 8A, mounting device 110 includes a support member 111 comprising an elongated shaped member, and a cross-member 112 rotatably mounted to support member 111. In various examples, the orientation of crossmember 112 may be changed by rotating cross-member 112 relative to an orientation of support member 111, as illustratively represented by double-headed arrows 113. In various examples, cross-member 112 has a first gripper 112A located at a first end of cross-member 112, and a second gripper 112B located at a second end of cross-member 112 opposite the first end of the cross-member.

In addition, cross-member 112 is adjustable with respect to a dimension between the first gripper 112A and the second gripper 112B, in the directions indicated by dimension 115. In various examples, cross-member 112 is configured to receive an electronic device, such as a smartphone, in the area between grippers 112A and 112B, and then to be adjusted along dimension 115 so that grippers 112A and 112B engage and secure the electronic device in a fixed position relative to cross-member 112. Because of the adjustability of cross-member 112, mounting device 110 may be configured to accept a range of sizes of electronic devices, including a range of sizes of devices such as smartphones, personal digital assistant (PDA), or other electronic devices that may be programmed and used as part of a 3D shoulder measurement system as described herein and any equivalents thereof.

FIG. 8B illustrates an example of mounting device 110 having received and secured an electronic device 16 via grippers 112A and 112B and cross-member 112. In various examples, electronic device 16 may be configured to perform any of the measurement procedures, and to provide any of the functions described throughout this disclosure with respect to calibration, measurement, communication, and/or data collection and generation, and any equivalents thereof. For example, once electronic device 16 is secured in mounting device 110, a user (not shown in FIGS. 8A-8B) may position the mounting device 110 including electronic device 16 to perform any of the measurements related to a patient's scapula and/or humeral elevations, as described throughout this disclosure, and any equivalents thereof.

Various examples of mounting devices have been illustrated and described above for use in securing an electronic device for the purpose of taking measurements related to positions/orientations of a patient's scapula and/or humerus. However, in various examples, an electronic device may be positioned by a user, for example on a patient's scapula or humerus, without the aid of a mounting device. For example, a user may simply align an edge, for example an edge following a longitudinal side of an electronic device, in a position relative to landmarks associated with the patient's scapula and/or humerus, and actuate the electronic device to take measurements related to the current alignment/orientation of the electronic device. Thus, in some examples having the electronic device that is programmed to perform the measurement procedure(s) secured in another mounting device is not necessarily required in order to perform one or more of the measurement procedures described throughout this disclosure, or any equivalents thereof.

Figure 9:
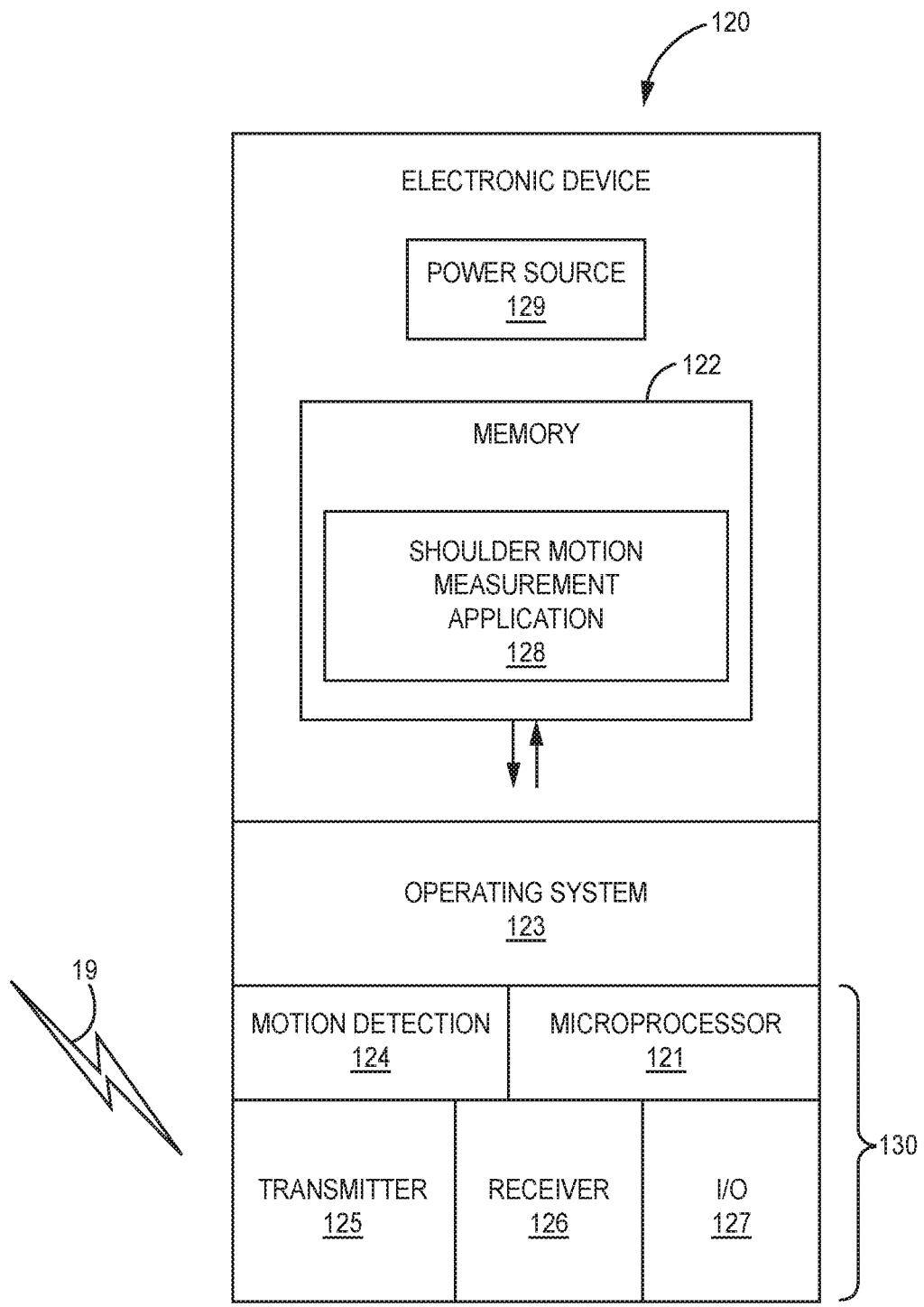
FIG. 9 is a block diagram illustrating an example of an electronic device, such as a mobile device, including but not limited to a smartphone, that may be configured to operate in accordance with various techniques described in this disclosure.

FIG. 9 is a block diagram illustrating an example of an electronic device 120, such as a mobile device, including but not limited to a smartphone, that may be configured to operate in accordance with various techniques described in this disclosure. In various examples, electronic device 120 is electronic device 16 as illustrated and described with respect to any of FIGS. 1A, 1D-1E, 4A-4D, 5B, 6B, 7B, 8B, 10, and 18. In various examples, electronic device 120 is configured to perform one or any combination of the functions, and to incorporate any of the features ascribed throughout this disclosure to electronic devices, including electronic device 16, and any equivalents thereof.

In the example illustrated in FIG. 9, electronic device 120 includes various hardware components, such as electronic circuitry, that provide core functionality for operation of the device. For example, electronic device 120 includes one or more programmable processors 121 (e.g., processing circuitry) configured to operate according to executable instructions (i.e., program code), typically stored in a computer-readable medium or data storage such as static, random-access memory (SRAM) device or Flash memory device, generally indicated as memory 122 in FIG. 9. I/O 127 may include one or more devices, such as a keyboard, camera button, power button, volume button, home button, back button, menu button, provided either as actual hardware or as graphically generated devices, as would be understood by one of ordinary skill in the art. Transmitter 125 and receiver 126 provide wireless communication with other devices, such as a cloud server, computer system, additional sensor, or other mobile device via a wireless communication link 19 as described for example with respect to electronic device 16 and FIG. 1A, such as but not limited to high-frequency radio frequency (RF) signals.

Electronic device 120 may include additional discrete digital logic or analog circuitry not shown in FIG. 9. Electronic device 120 may include an operating system 123 that executes on the one or more processors 121, and provides an operating environment for one or more user applications (commonly referred to as "apps"), including shoulder motion measurement application 128, which may be downloaded to electronic device 120 for example through receiver 126, and stored in memory 122. Applications may, for example, comprise executable program code stored in computer-readable storage device for execution by the one or more processors 121. As other examples, the user applications may comprise firmware, or in some examples, may be implemented in discrete logic included in electronic device 120.

Electronic device 120 also includes a motion detection unit 124 arranged to detect movement and/or orientation of the electronic device, and may also include an image capture device. The motion detection unit 124 can include various sensors, for example, motion sensors, accelerometers, gyroscopes, and other sensors, as would be understood by one of ordinary skill in the art, each sensor configured to provide one or more output signals related one or more parameters being sensed by the sensor. In some cases, these output signals correspond to sensed parameters related to orientation, speed, distance, or the other relevant movement data incurred by the electronic device 120. Such data can be used and processed by shoulder motion measurement application 128 in whole or in part to provide any of the calibration and/or measurement features and functions described throughout this disclosure, and any equivalents thereof.

Electronic device 120 in various examples includes power source 129, comprising a device such as a battery and/or a storage capacitor, that is arranged to store electrical power, and that is coupled to the other devices of electronic device 120 to provide electrical power for the operation of the circuitry comprises these devices. In various examples, power source 129 includes additional circuitry, such as recharging circuitry, voltage regulation circuitry, and/or filter circuitry that allows for control and regulation of various power levels required to be powered from power source 129. For example, recharging circuitry may be provided as a part of power source 129 to allow recharging, inductively and/or by a wired connection, of the power source by one or more external charging devices (not shown in FIG. 9). The additional circuitry such as voltage regulation circuitry and/or filter circuitry may regulate and provide one or more levels of electrical power, provided in the required waveforms and/or within the required range(s) of electrical parameters, to properly operate the electronic circuits of electronic device 120, as would be understood by one of ordinary skill in the art.

FIGS. 10A-10B illustrate an example process by which a user interacts with a shoulder motion measurement system according to various techniques described in this disclosure. In various examples, the process illustrated in FIGS. 10A-10B may be used to choose various parameters, including capture parameters, and/or to calibrate the motion measurement system. Screens 132, 136, and 140, or variations of these screens, may be generated and displayed on an electronic device, such as electronic device 16 or electronic device 120, following downloading of the shoulder motion measurement application(s) to the electronic device. Upon running the application(s), screen 132 may initially be generated and displayed by the electronic device. Screen 132 includes an information bar 135 that may display information related to the subject matter being displayed at the time, and may include one or more graphically generated selectable option buttons, that may be actuated by the user, for example by touching the screen in the area of the screen that includes the selectable option. As shown, screen 132 includes an indication that the screen related to "Clients." Screen 132 also includes a "Enter client identification" block 133 that includes a fillable field that allows a user to enter a client number. Screen 132 also includes a graphically generated numeric keypad 134 that allows a user to enter numerical information, for example a client identification number, into the fillable field of block 133. Keypad 134 may be configured to allow a user to enter the numeric information by touching the appropriate portions of the keypad 134 as would be understood by one of ordinary skill in the art. In addition, information bar 135 may include a selectable option button that allows a user, when the button is actuated, to indicate that the user wishes to add a new client that for example may not already have an assigned client number. Information bar 135 may also include an "Exit" button that allows a user to exit screen 132 when the exit button is actuated.

Once a valid client identifier number has been entered into the fillable field of block 133, the user may actuate the "Continue" button located within block 133 to proceed to screen 136. As shown, screen 136 includes information bar 135 providing a "Cancel" and a "Next" selectable option. Screen 136 further includes an information block 137 that provides a user with information and instructions on the additional selections that can be provided by the user through screen 136. The user interface of screen 136 allows the user the choice to record humeral elevation in multiple planes. On screen 136 the user may choose the plane of humeral elevation he/she plans to measure at block 139. For example, screen 136 allow a user to indicate a plane, such as sagittal for shoulder flexion measurements, frontal for shoulder abduction measurements, and scapular for scapular plane abduction measurements. Screen 136 also allows the user to choose the side of the patient they plan to measure at block 138, e.g., "left" side, "right" side. In some examples, block 138 may include additional options, for example an option to select "both" sides related to which sides of the patient the uses plans to take measurements from. In various examples, selection of the desired option in block 138 an/or block 139 may be indicated by the selection option being displayed in a different color, for example black with white letters, as opposed to the un-selected option(s) being displayed in black letters on a white background, although the indication of the selected option is not limited to these or any other particular formats for indication of a selected option within screen 136.

Once the user has indicated on screen 136 the desired options, the user may actuate the "Next" button on the information bar 135 in order to have the electronic device 16 generate and display the next screen. In some examples, the next screen displayed is screen 140. As shown in screen 140, the information bar 135 now displays the word "Calibration," to indicate that screen 140 is displaying information related to the calibration of the electronic device. As shown, screen 140 includes an information block 141, a graphically generated image 142, and a "Calibrate" selection button 143. Information block 141 may include text that instructs the user on how to position the electronic device in preparation for calibration. In various examples, the graphical image 142 provides an image of a user positioning an electronic device, for example on a wall with the bottom edge parallel to the ground, in order to further illustrate for the user how to position the electronic device for calibration. Once the user has positioned the electronic device based on the instructions provided on the display, the user may actuate the "Calibrate" button, for example by touching the display of the electronic device in the area of the "Calibrate" button, to indicate to the electronic device that the electronic device is in position for calibration. Once the actuation of the "Calibrate" button has been detected by the electronic device, the electronic device may then proceed with running the calibration procedure in order to calibrate any internal processes associated with using the electronic device to take shoulder motion measurements, and/or to calibrate any of the one or more sensors located within the electronic device in preparation for taking shoulder motion measurements.

FIG. 10B is an illustration of a user's hands positioning and holding an example motion monitoring system 10 on a wall 146 while the user is positioned for viewing the various screens, including screen 140, as part of performing the calibration procedure described above with respect to FIG. 10A.

Figure 11:
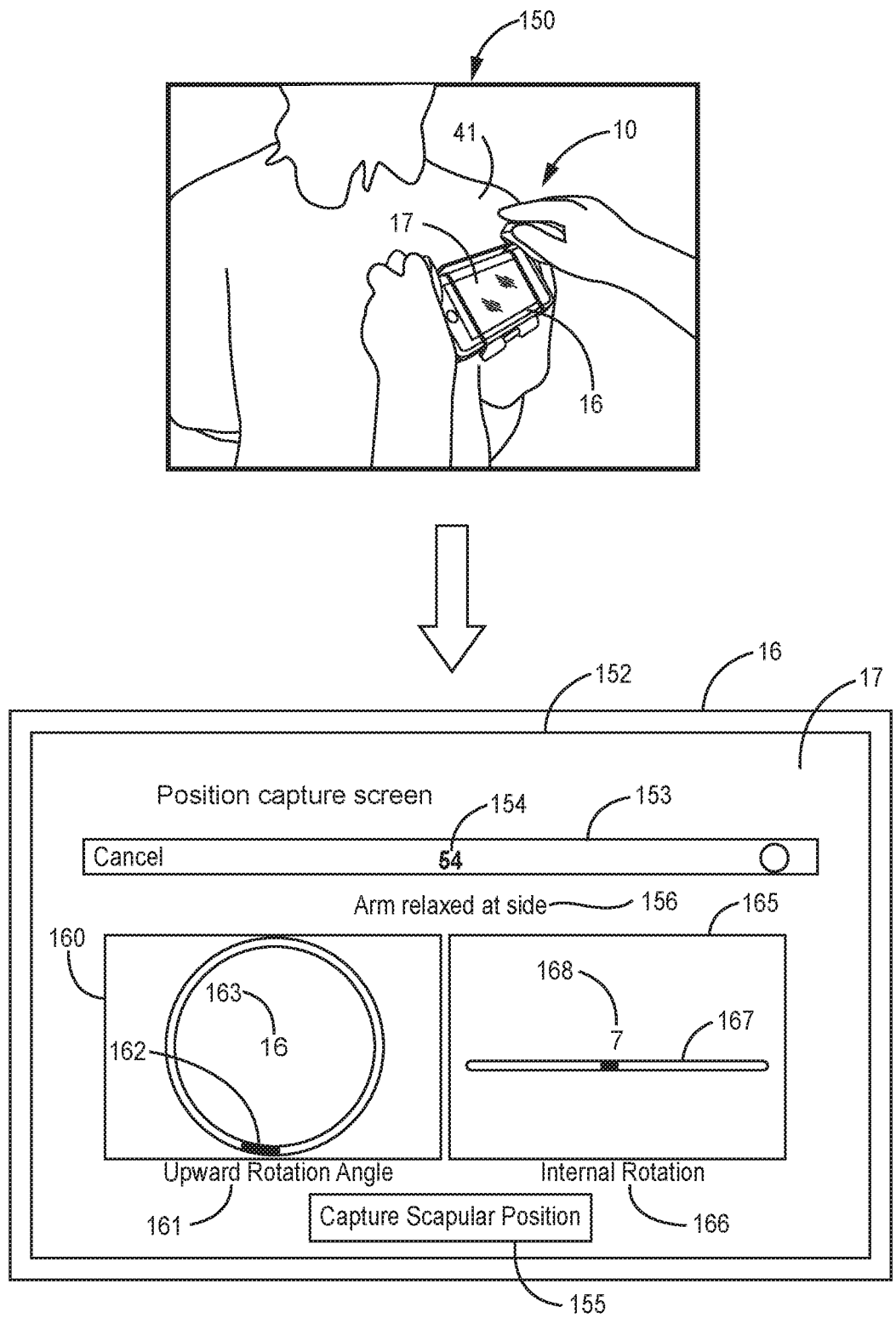
FIG. 11 is a diagram illustrating an example use of a motion measurement system aligned to a scapula of a patient, and a screen generated and displayed by a display of the system, in accordance with various techniques described in this disclosure.

FIG. 11 is a diagram 150 illustrating an example use of a motion measurement system 10 aligned to a scapula of a patient 41, and a screen 152 generated and displayed by display 17 of the system based on measurements taken by the system in accordance with various techniques described in this disclosure. In various example, the motion measurement system 10 has previously been calibrated, for example using the calibration process illustrated and described with respect to FIG. 10. As shown in FIG. 11, system 10 may then be placed adjacent to the right scapula of patient 41, and aligned by the user (not fully shown in FIG. 11) for example as illustrated and described above with respect to FIGS. 1A-1E and FIG. 3. Referring again to FIG. 11, screen 152 is an example of a screen that may be generated by and displayed by the electronic device 16 of system 10 at various points during the measurement procedure illustrated in FIG. 11.

Screen 152 in various examples includes an information bar 153 that may include information, such as a patient identification number 154 associated with patient 41 for which the measurement process and the collected data associated with the measurement process are measured for. Information bar 153 may also include one or more selectable buttons that allow a user to provide inputs to electronic device 16, for example by touching the display in the area of the button. As shown in FIG. 11, information bar 153 includes a "Cancel" button that allows a user to exit screen 152 when the button is actuated. Information bar 153 also includes an information Icon associated with information such that when the information Icon is actuated, in some examples provides access to information displayed on the screen that may be useful in providing instructions to the user with respect the one or more features and functions of the system, including information that may be applicable to the current procedure that is being provided through the use of screen 152.

Screen 152 in various examples includes a "Capture Scapula Position" button that may be actuated by the user, for example by touching the display 17 in the area of screen 152 that displays button 155. In various examples, when the user has aligned system 10 in the desired position relative to the patient 41, the user may actuate button 155 to indicate to the electronic device 16 that the system is positioned in the desired manner, and that the user wants the system to take measurements. In various examples, once button 155 is actuated, the electronic device 16 performs the measurement process, and in some examples, using one or more of the sensors located within electronic device 16, measures one or more parameters associated with the patient based on the position and/or orientation of system 10 at the time button 155 was actuated. Upon completing of making the measurements, the data may be processed, for example by the one or more processors located within electronic device 16, in order to generate and display the measurement boxes 160 and 165 shown as part of screen 152.

In various examples, measurement box 160 includes an information footer 161 indicating that box 160 is displaying graphical information related to the "Upward Rotation Angle" of the patient's scapula. Measurement box 160 further includes a graphical display including a graphical indicator 162 that provides an indication of the measured data related to the "Upward Rotation Angle" of the measured scapula position for patient 41. In addition, measurement box 160 may also include a display of a numerical value 163 that provides a value for the measured degrees of scapula upward rotation as measured for patient 41. As shown, a measured value of "16" degrees of scapular upward rotation is displayed for numerical value 163. Measurement box 165 includes a graphical display including a graphical indicator 167 that provides an indication of the measured data related to the "Internal Rotation" of the measured scapula position for patient 41. In addition, measurement box 165 may also include a display of a numerical value 168 that provides a value for the measured internal rotation. As shown, a measured value of "7" is displayed at numerical value 168 representative of a measured scapular internal rotation for the patient's scapula when their arm is relaxed at the side. The actual values shown in FIG. 11 are illustrative and non-limiting, wherein examples of the values and the ranges of values that may be displayed by user interface screen 152 are not limited to these illustrated values, as would be understood by one of ordinary skill in the art.

In various examples, during shoulder motion measurement, illustrated in FIG. 11, displays provided on screen 152 guide the user through the following exemplary process:
1. Placing the electronic device 16 into receptacle 20 as shown.
2. Pulling the strap or clip around the electronic device to secure the electronic device in the mounting device 12
3. Holding the system 10 against the patient 41.
4. Utilizing the onscreen instructions for identifying the patient's scapula positions.

To measure the patient's values and compare the values to existing data, the measurement system 10 measures the patient scapular and humeral angles in three arm positions, for example with the arm relaxed at the side (rest), with the arm elevated to 90-degrees in the chosen plane (palm forward and thumb up), and with the arm fully elevated in the chosen plane (palm forward and thumb up).

Arm Relaxed at Side, Scapular Position Capture:
1. With the patient's arms relaxed at their side, the user positions the patient so their trunk is facing parallel to the same wall used to calibrate, but so the patient can still move their arms without obstruction.
2. Integrate the electronic device with the mounting device: Place the electronic device into the mounting device in the same orientation as it was in the calibration step. The electronic device should rest on the body of the scapula with the grips on top when using a mounting device such as mounting device 12 shown in FIG. 1A, or using the finger holes for example as provided in system 50 shown in FIG. 4A.
3. Using the grips or the finger holes provided with the system being used, place your finger as close to the root of the spine of the scapula as possible. Place another finger as close as possible to the posterior lateral acromion. Allow the measurement system to rest against the body of the scapula.
4. Push any part of the display screen to capture the position of the scapula at rest.
5. Some samples may also include a Humeral Elevation Position Capture: Move the measurement system so the long axis of the handle is parallel to the shaft of the humerus of the patient, and push any part of the screen to capture the humeral elevation angle with the arm relaxed at the side.

90° Humeral Elevation, Scapular Position Capture:
1. Have the patient raise their arm perpendicular to the body in the chosen plane of motion (palm forward and thumb up). Find the same landmarks on the root of the spine of the scapula and posterior lateral acromion with the user's fingers; rest the shoulder motion measurement system against the body of the scapula of the patient.
2. Push any part of the screen to capture the position of the scapula with the arm perpendicular to the body.
3. Some examples may include-Humeral Elevation Position Capture: While the patient maintains their arm in the perpendicular position, move the Shoulder motion measurement system so the long axis of the handle is parallel to the shaft of the humerus of the patient, and push any part of the screen to capture this humeral elevation angle.

Arm fully elevated, Scapular Position Capture:
1. Have the patient raise their arm in the chosen plane of motion, palm forward and thumb up. Find the same landmarks on the root of the spine of the scapula and posterior lateral acromion with your fingers; rest the shoulder motion measurement system against the body of the scapula.
2. Push any part of the screen to capture the position of the scapula with the arm fully elevated.
3. Some examples may include-Humeral Elevation Position Capture: While the patient maintains their arm in the fully elevated position, move the shoulder motion measurement system so the long axis of the handle is parallel to the shaft of the humerus of the patient, and push any part of the screen to capture this humeral elevation angle.

Figure 12:
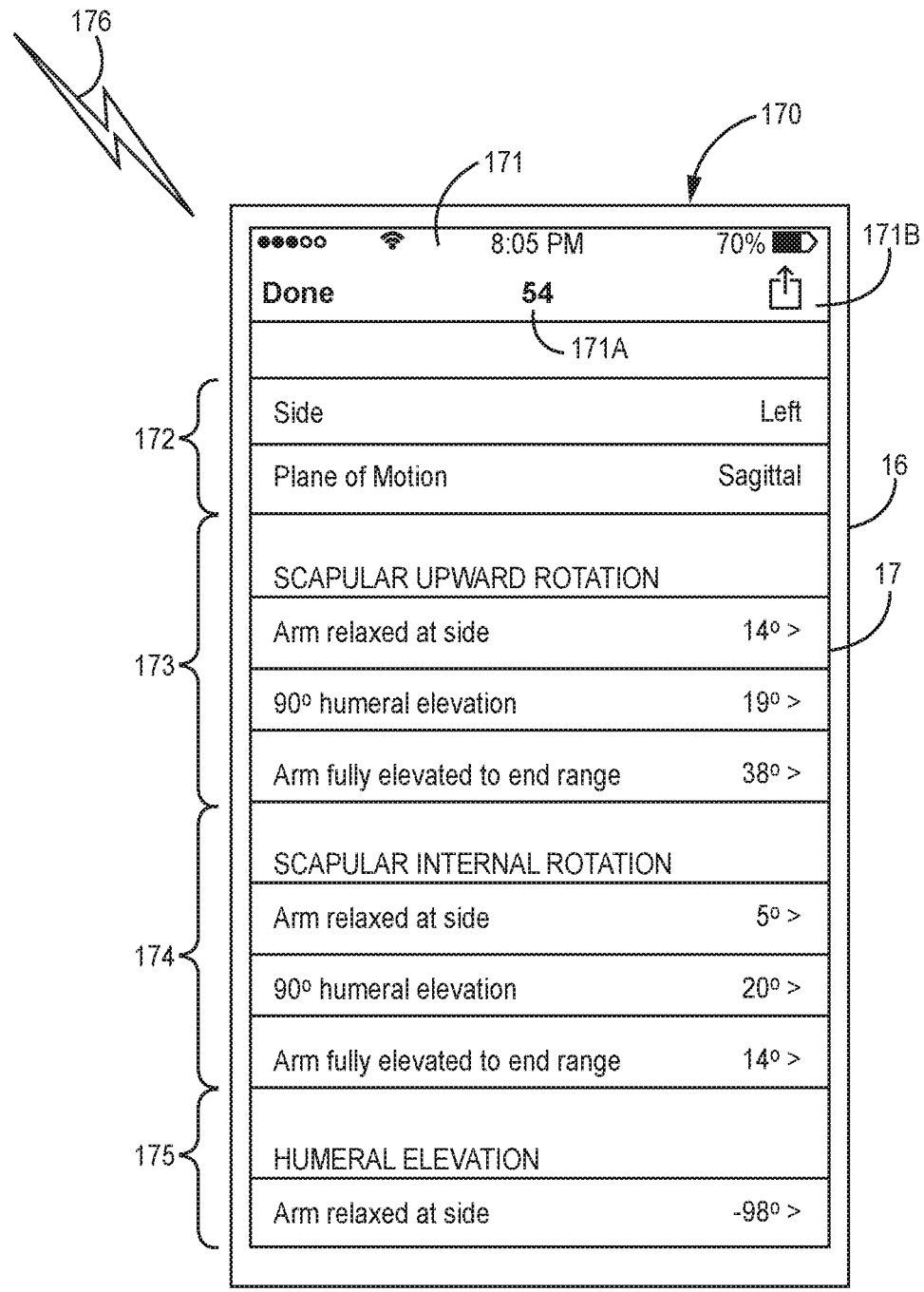
FIG. 12 illustrates an example user interface screen presented by an electronic device in accordance with various techniques described in this disclosure.

FIG. 12 illustrates an example user interface screen 170 presented by electronic device 16 in accordance with various techniques described in this disclosure. As shown, user interface screen 170 includes an information bar 171, and a plurality of display blocks 172, 173, 174, and 175, that may be displayed on a display of the electronic device 16. Information bar 171 may include an indication of the client identification number 171A, for example client identification number "54" that identifies the client to which the data being displayed is associated with. Information bar 171 may also include other information, such as the strength of a wireless communication connection, date/time information, and an indication of the state of charge of a device such as a battery included within and powering the electronic device. Information bar 171 may also include one or more selectable buttons, such as button 171B, that may be actuated by a user, for example by the user touching the display providing user interface screen 170 in the area of the button. In various examples, button 171B may be an icon that when actuated by the user, causes the electronic device providing user interface screen 170 to format and transmit the data associated with screen 170 to one or more external devices (not specifically shown in FIG. 12), via a communication link, such as communication link 19 as described for example with respect to electronic device 16 and FIG. 1A, such as but not limited to high-frequency radio frequency (RF) signals. External devices may include any of the devices, such as computers, servers, and devices coupled to computer networks and/or the Internet, as illustrated and described with respect to external devices 29 and FIG. 1A.

Examples of data displayed as part of user interface screen 170 may include information block 172 displaying information related to which side and what plane of the patient the additional data associated with user interface screen 170 was measured from. Blocks 173, 174 and 175 may include data related to different values actually measured for the patient having patient identification number 54 with the patient's arm in different arm positions. For example, block 173 displays measured values associated with patient's scapula upward rotation when the patient's arm was located at the relaxed at side, at ninety degrees, and at a fully elevated to an end range position. Block 174 displays measured values associated with the patient's same three arm positions, but for the scapula internal rotation positions. Block 175 displays a value associated with a measured value of the humeral elevation of the patient when the patient's arm when in the relaxed at the side position. In some examples, the additional data for measured values associated with humeral elevations when the patient arm was at other positions may be brought into view by having the user actuate the display in order to cause screen 170 to scroll in an upward and downward direction, for example using a gesture motion on the display, as would be understood by one of ordinary skill in the art.

The actual values shown in FIG. 12 are illustrative and non-limiting, wherein examples of the values and the ranges of values that may be displayed by user interface screen 170 are not limited to these illustrated values, as would be understood by one of ordinary skill in the art.

Figure 13:
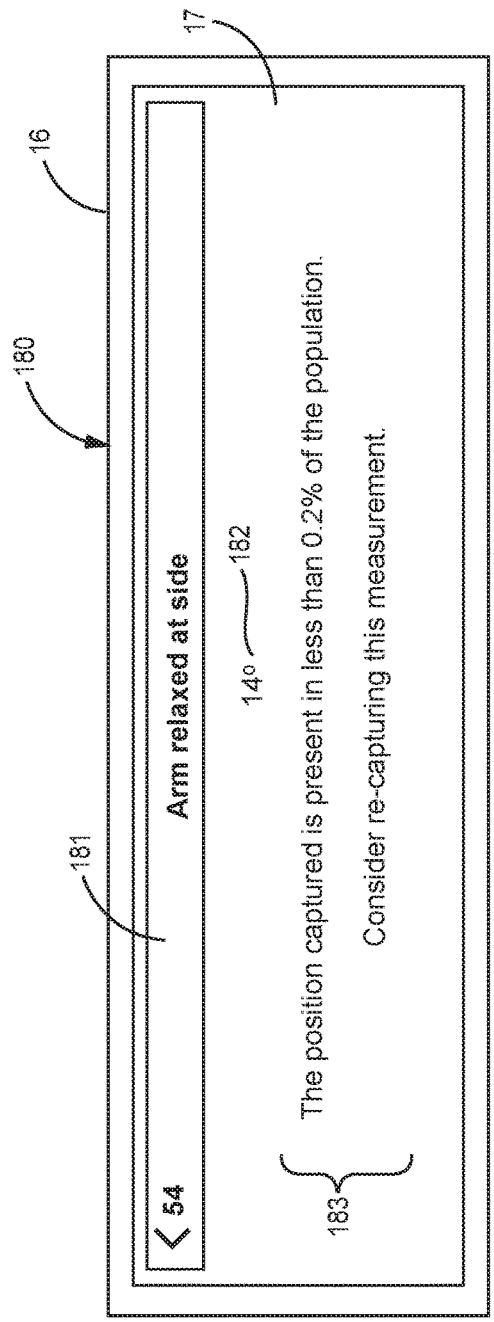
FIG. 13 illustrates an example user interface screen presented by an electronic device in accordance with various techniques described in this disclosure.

FIG. 13 illustrates an example user interface screen 180 presented by an electronic device in accordance with various techniques described in this disclosure. In some examples, screen 180 may be automatically presented on display 17 of electronic device 16 during a measurement procedure and upon the electronic device determining that the captured position data indicates a position below a configurable threshold, such as a position present in less than 0.2% of a population. This feature is an error checker which prompts the user that their measurement is likely in error and they should reconsider data capture. As shown in screen 180, a numerical value 182 of "14°" is displayed as a measured value for some patient related measurement process. The instruction block 183 includes text explaining the relevance of this measured value along with a suggestion to consider re-capturing this measurement. The information bar 181 displayed as part of screen 180 indicates to a user that the measurement at issue was taken when the patient's arm was relaxed at the patient's side. The actual value or values shown in FIG. 13 are illustrative and non-limiting, wherein examples of the values and the ranges of values that may be displayed by user interface screen 180 are not limited to these illustrated values, as would be understood by one of ordinary skill in the art.

Figure 14:
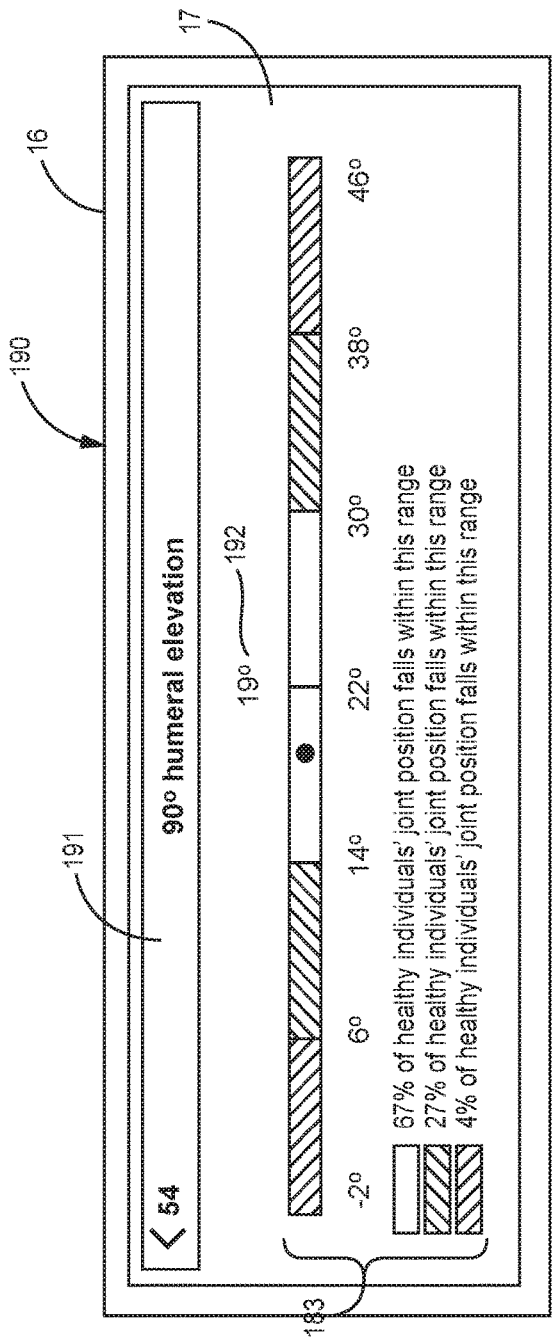
FIG. 14 illustrates an example user interface screen presented by an electronic device in accordance with various techniques described in this disclosure.

FIG. 14 illustrates an example user interface screen 190 presented by an electronic device in accordance with various techniques described in this disclosure. In some examples, screen 190 may be generated and displayed by a display 17 of electronic device 16 to output results of a comparison of the patient's data to configured thresholds and categories. In this example, electronic device 16 constructs and outputs screen 190 to illustrate a position of results captured from the current patient along a spectrum of joint position categories. As shown in the example illustrated in FIG. 14, the current patient has been determined to have numerical value 192 of "19°" for humeral elevation, and the output screen shows this value to be within a range associated with 67% of healthy patients via display block 193. Information bar 191 includes an indication that the measurement is in relationship to a "90° humeral elevation" measurement. This type of data presentation may assist the user in interpretation of the patient's data, and thus assist the user or other professional with diagnosis and treatment planning for the patient associated with this measurement. The actual values shown in FIG. 14 are illustrative and non-limiting, wherein examples of the values and the ranges of values that may be displayed by user interface screen 190 are not limited to these illustrated values, as would be understood by one of ordinary skill in the art.

Figure 15:
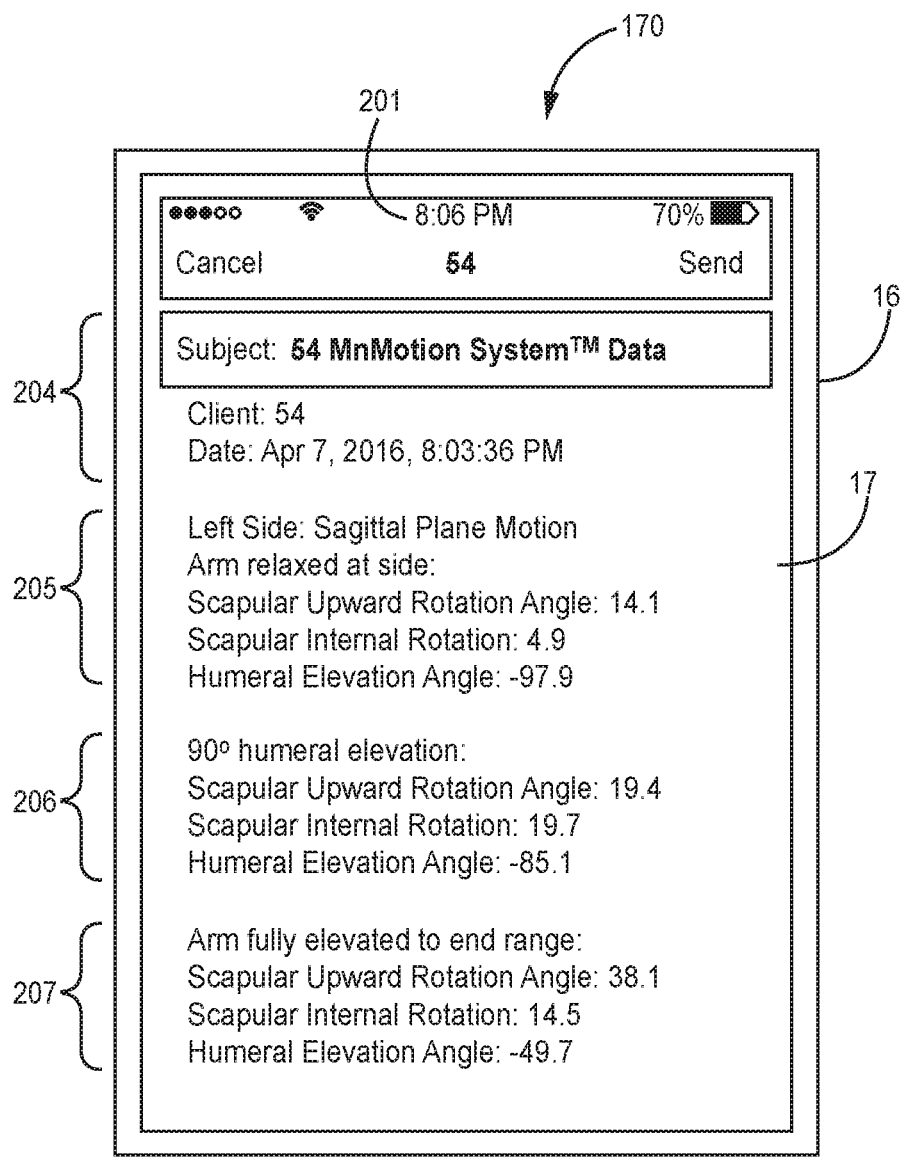
FIG. 15 illustrates an example user interface screen presented by an electronic device in accordance with various techniques described in this disclosure.

FIG. 15 illustrates an example user interface screen 200 presented by an electronic device in accordance with various techniques described in this disclosure. In various examples, screen 200 displays information bar 201, patient information block 204, and information blocks 205, 206, and 207, showing scapula upward and internal rotation angles, and humeral elevation angles for the patient associated with the patient data displayed at block 204. In various examples, screen 200 displays data that may be included in an email output of scapula/humeral positions and angles, and/or as a spreadsheet file generated by the software application to report the results.

Measurement data displayed in block 205 includes measurements for scapula upward rotation, scapula internal rotation and humeral elevation angle taken when the patient's arm was relaxed at the patient's side. Measurement data displayed in block 206 includes measurements for scapula upward rotation, scapula internal rotation and humeral elevation angle taken when the patient's arm was at a 90° humeral elevation. Measurement data displayed in block 207 includes measurements for scapula upward rotation, scapula internal rotation and humeral elevation angle taken when the patient's arm was at a fully elevated to end range position. In some examples, the "fully elevated to end range" elevation represents the highest or greatest level of extension the patient was able to move the arm to relative to the relaxed at side position. The actual values shown in FIG. 15 are illustrative and non-limiting, wherein examples of the values and the ranges of values that may be displayed by user interface screen 200 are not limited to these illustrated values, as would be understood by one of ordinary skill in the art.

Figure 16:
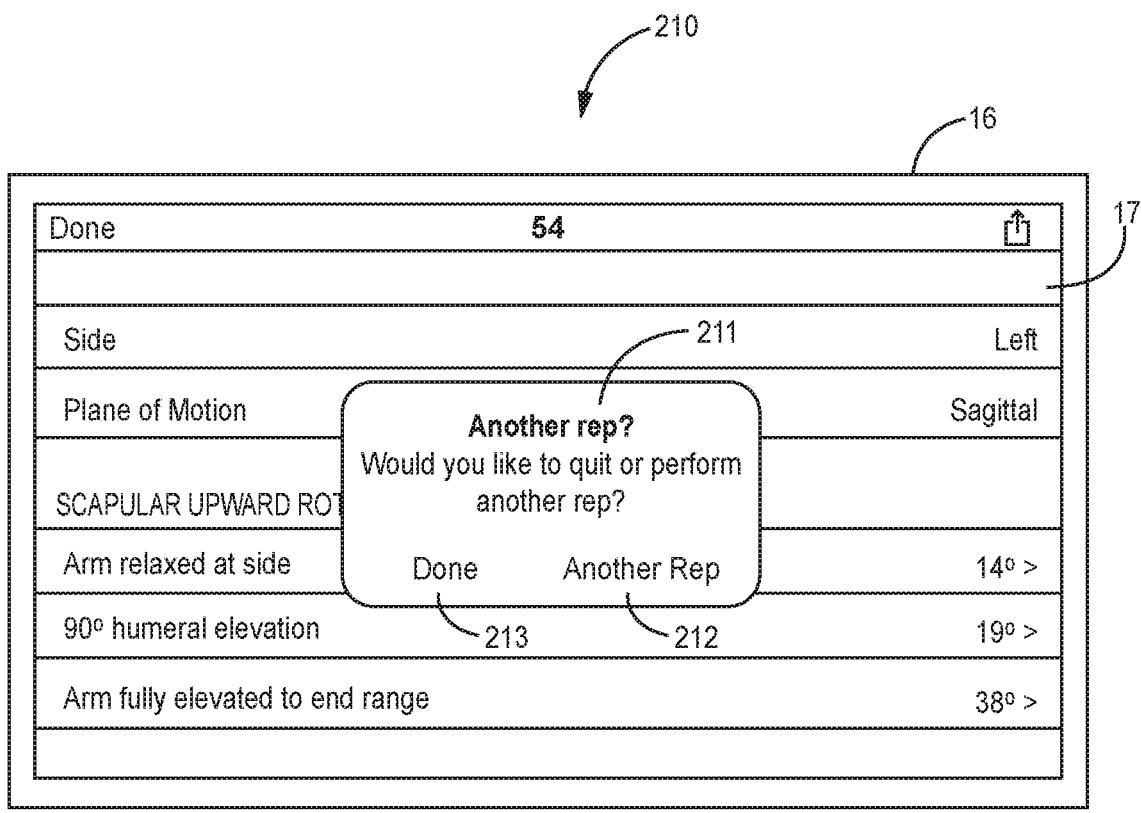
FIG. 16 illustrates an example user interface screen presented by an electronic device in accordance with various techniques described in this disclosure.

FIG. 16 illustrates an example user interface screen 210 presented by an electronic device in accordance with various techniques described in this disclosure. In various examples, screen 210 may be generated by an electronic device and displayed on the display 17 of the electronic device at various stages of a measurement process to query whether the user wishes to perform another repetition and capture another position. Screen 210 as illustrated includes "Another rep?" block 211, which includes selectable "Another Rep" button 212 and a selectable "Done" button 213. In various examples, when block 211 appears on the display 17, a user may indicate that they wish to take additional measurement(s) as part of a given measurement procedure by selection of the "Another Rep" button 212. Upon electronic device 16 receiving an indication of actuation of button 212, the electronic device may generate a new screen that allows the user to proceed with another measurement. In the alternative, actuation of the "Done" button 213 may indicate that the user does not wish to proceed with another measurement procedure, at least not based on the current set of measurement parameters. Upon electronic device 16 receiving an indication of actuation of button 213, electronic device 16 may generate a new screen that allows the user to terminate the measurement procedure, or for example to enter new measurement parameters for additional measurements to be taken on a same or a different patient.

Figure 17:
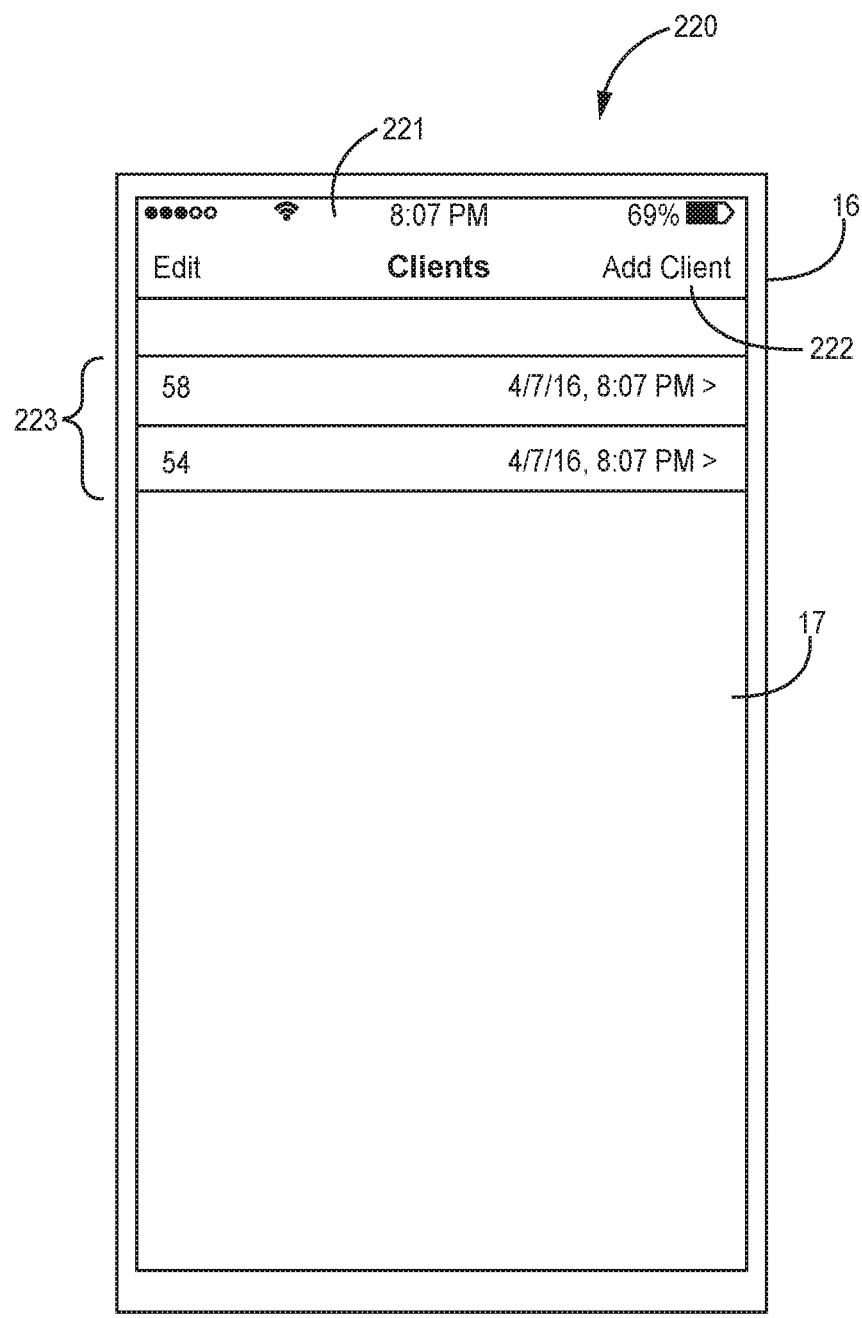
FIG. 17 illustrates an example user interface screen presented by an electronic device in accordance with various techniques described in this disclosure.

FIG. 17 illustrates an example user interface screen 220 presented by an electronic device in accordance with various techniques described in this disclosure. In various examples, screen 220 may be generated by an electronic device 16 and displayed by display 17 to present a client list 223 with de-identified (e.g., anonymous) code numbers for each client. By interacting with the interface, an authorized system user can add and/or remove clients or add and/or remove capture positions for a specific client.

Figure 18A:
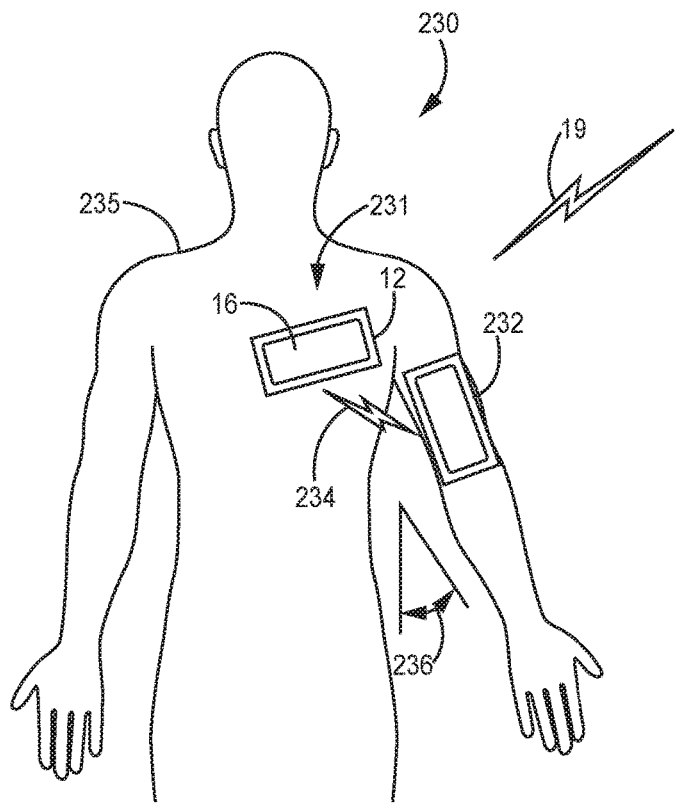
FIGS. 18A-18B are diagrams of a motion measurement system illustrating use of a paired application for shoulder motion measurements in accordance with various techniques described in this disclosure.
Figure 18B:
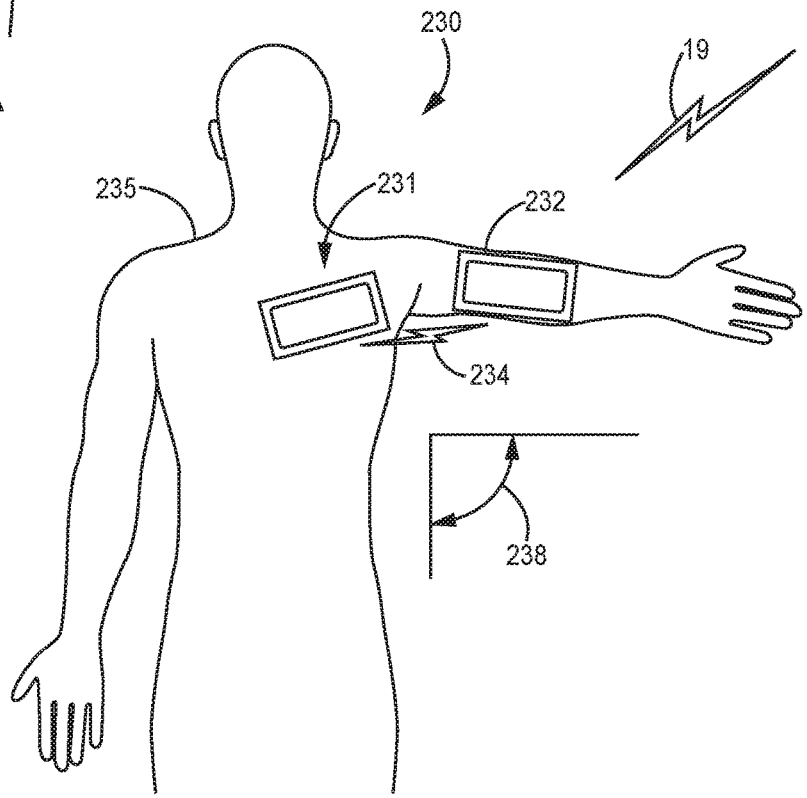

FIGS. 18A-18B are diagrams of a motion measurement system 230 illustrating use of a paired application for shoulder motion measurements in accordance with various techniques described in this disclosure. As shown in FIG. 18A, a first shoulder motion measurement system 231 is configured to be arranged adjacent to a scapula of patient 235, and to run the measurement applications(s) as described throughout this disclosure, but in conjunction with a second motion measurement system 232. The first shoulder motion measurement system 231 may include any of the mounting devices, such as mounting device 12, and an electronic device secured to the mounting device, such as electronic device 16, as described throughout this disclosure, and any equivalents thereof. In addition, system 231 is further configured to communicate via communication link 234, to the second motion measurement system 232 as part of the measurement procedures being performed by system 230.

In various examples, system 232 includes a second electronic device, for example a smartphone, that has programming downloaded to the electronic device, and that includes one or more sensors that allow the electronic device of system 232 to measure data related to the current arm position of patient 235 as part of a measurement procedure being performed on patient 235. In various examples, system 232 is attached for example using straps (not shown in FIG. 18A) to an upper arm area of patient 235 that corresponds to the same side (i.e., right side, left side) of patient 235 that system 231 is being positioned on for the purpose of taking motion measurements. In various examples, both system 231 and system 232 have been calibrated, for example using the calibration procedure(s) described through the disclosure, or using any equivalents thereof. In addition, system 231 and system 232 have be synchronized to one another to allow for the timing of taking measurements and the transfer of data between the electronic devices of the systems, as further described below. In various examples, the communications between system 231 and system 232 may be accomplished via wireless communications, such as but not limited to use of Bluetooth® technology.

In various examples, the second motion measurement system 232 may be configured to measure an actual humeral elevation upon request from the first motion measurement system 231, and to provide the measured humeral elevation, for example in the form of a value for angle 236, to the first motion measurement system 231 as part of a motion measurement process being performed on patient 235. In various examples, second motion measurement system 232 uses sensor(s) within the electronic device of system 232 to sense the elevation angle of the patient's arm based on sensing the orientation of the patient's arm to which system 232 is attached relative to gravity. A user (not shown in FIG. 18A) may, following calibration and synchronization of systems 231 and 232, position system 231 adjacent to the right scapula and at the desired position for taking a shoulder motion measurement, using any of the positioning techniques described throughout this disclosure, or any equivalents thereof. As shown in FIG. 18A, the right arm of patient 235 to which system 232 is attached is oriented at angle 236 relative for example to gravity, and may be considered to be an arm position classified as relaxed and resting at the patient's side.

Once system 231 is positioned in the desired location relative to patient 235, the user may actuate system 231 to request that system 230 initiate taking measurements related to the position of the right scapula of the patient. In addition, system 231 may communicate with system 232, requesting that system 232 make measurements, and in some examples to process these measurements to determine the current value for angle 236 associated with the orientation of the right arm of patient 235. Upon receiving the request to take measurements, system 232 is configured to sense a position/orientation of the electronic device included in system 232, and thus the angle measurement requested by system 231. System 232 is then configured to automatically transmit data related to the measured position/orientation of the patient's right arm back to system 231. System 231 receives the information transmitted by system 232, and incorporates the date related to the angle of the patient's right arm to the measurements taken by system 231 at that same time. By automating the process of taking the scapula measurements using system 231 with taking the measurements related to the angle of the humerus of the arm of the patient 235 associated with the same side of the patient where the scapula measurements are being taken using system 232, a measured humeral angle, as opposed to an estimate of the angle made for example by the user, can be incorporated into the measurement data. The measurement of the angle related to the humerus increases the overall accuracy of the data being collected when these measurements are being taken, for example by eliminating the error of having the user try to estimate the angle of the patient's arm during the measurement process.

FIG. 18B illustrates another possible positioning of a patient's right arm that can be provided by having the patient move his/her arm from the position shown in FIG. 18A (e.g., a position near the patient's side) to the position shown in FIG. 18B (e.g., a ninety-degree orientation relative to the patient body and/or to gravity). In FIG. 18B, a same or similar measurement process may be performed on patient 235 as was described above with respect to FIG. 18A, but with the patient's arm in the ninety-degree orientation shown in FIG. 18B. As part of the measurement process illustrated in FIG. 18B, system 231 may request that system 232 perform a measurement procedure to determine the measured value of angle 238, and to transmit data back to system 231 that includes a value or other data indicative of the measured angle of the patient's right arm at the time of the measurement process. In various examples, data capture is performed dynamically, for example at a sample rate of 100 Hertz.

In addition, system 231 may receive the data from system 232 related to the measurement angle of the patient's arm, and incorporating this data into the measurement data generated by system 231 related to the patient's scapula as part of the measurement process depicted in FIG. 18B. In various examples, when using the paired systems, a user will be prompted, for example by a prompt provided on the display of electronic device 16 of system 231, to synchronize to the patient device of system 232, in some examples using peer-to-peer connectivity. In some examples the user, usually a physician or clinician, will initial the synchronization process, confirming that calibration has been completed for both system 231 and 232.

Once the synchronization and calibration of the systems has been confirmed, the user initiates the "reps," for example by having the patient 235 assuming one or more arm positions, and/or making one or more movements of the arm between a first and a second different arm position as part of the measurement procedure. The humeral elevation angles may be captured by system 232 automatically as patient 235 completes a rep. The data related to these captured elevation angles may be transmitted and captured by the user application running on system 231, for example each time the patient completes a rep, and for example associated with the patient 235 positioned their arm at zero, ninety, or one hundred twenty degrees. Data provided by system 232 is combined with the associated data captured by system 231. The combined data may be reviewed by the user and/or the patient 235 via a display provided by system 231, for example using any of the graphical displays of user interface screens described herein, or any other forms of data display as would be appropriate for the types of data collected and generated through the shoulder motion measurement systems of FIGS. 18A-18B. For example, data displayed may include a graph of each scapula angle, upward rotation, internal rotation, and tilt as measured for one or more humeral elevations, for example thirty, sixty, ninety, and/or one hundred twenty degree humeral elevations, and may include data related to the highest humeral elevation the patient was able achieve in any given session.

In various examples, system 231 and/or 232 may be communicatively linked, such as via communication link 19 as described for example with respect to electronic device 16 and FIG. 1A, such as but not limited to high-frequency radio frequency (RF) signals, to one or more external devices (not specifically shown in FIGS. 18A-18B, but for example to external devices 29 shown in FIG. 1A). Data collected and/or generated by system 231 and/or by system 232 may be uploaded to these external devices, for example for storage, and/or for use by other users, for example by a physician, a clinician, or a physical therapist, who is not physically located in the same place as where these measurements were taken, but who can review the uploaded data for diagnostic and treatment planning purposes.

Figure 18C:
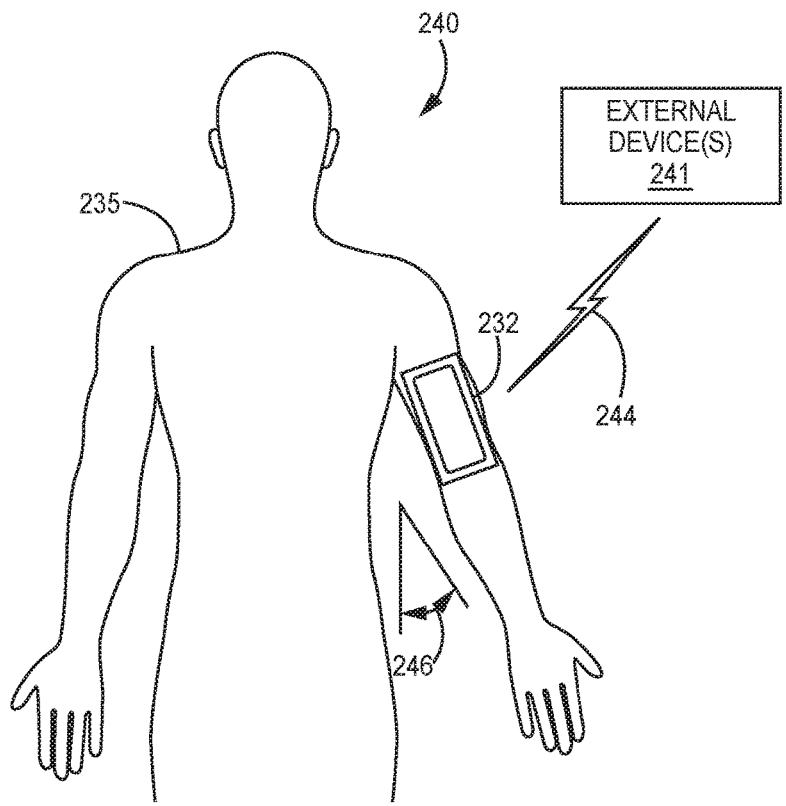
FIGS. 18C-18D are diagrams of a motion measurement system in accordance with various techniques described in this disclosure.
Figure 18D:
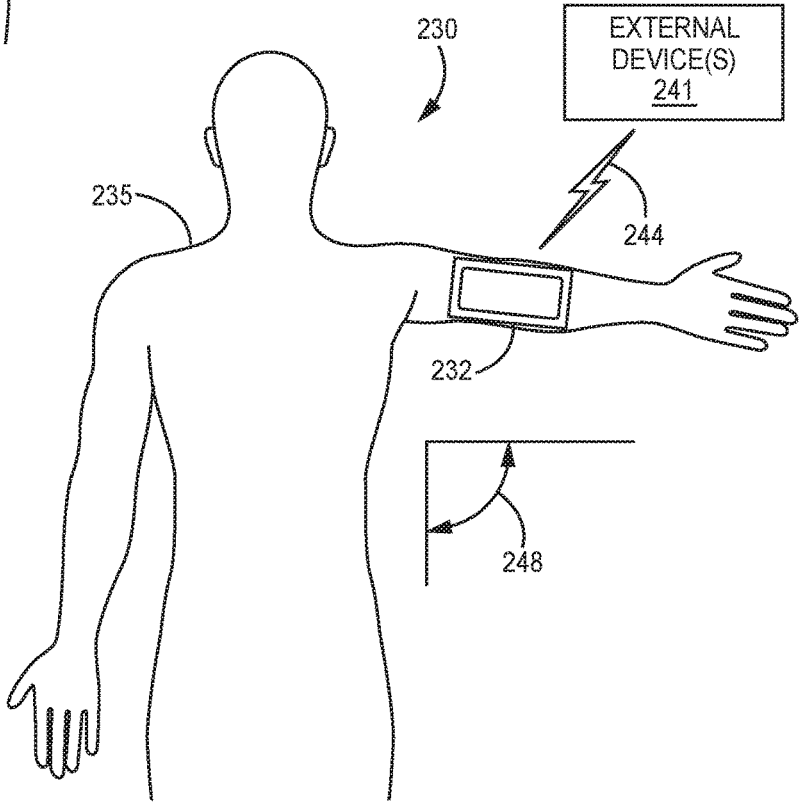

FIGS. 18C-18D are diagrams of a motion measurement system 240 in accordance with various techniques described in this disclosure. The measurement system 240 in some examples is configured to be operated by the patient 235 without direct assistance from another user, such as a physician or a clinician, and may for example be referred to as a "Home Use" portion of a shoulder motion measurement system.

As shown in FIG. 18C, a shoulder motion measurement system 232 is configured to be attached for example to an upper arm area of patient 235 in a manner similar to the use of system 232 described above. In addition, system 232 is further configured to communicate via communication link 244, to one or more external device(s) 241 through communications link 244. Communication link 244 is not limited to any particular type of communication formats or protocols, and may utilize any type of communication link that allows system 232 to communicate with the one or more external devices 241. In various examples, external device(s) 241 may include any type of device, such as a smartphone, a computer, such as a laptop computer, or a computing device coupled to a computer network, that is configured to run one or more application(s) associated with the "Home Use" version of system 232.

For example, external device(s) 241 may provide for downloading of the one or more applications that, when downloaded to system 232, allow system 232 to perform any of the functions and provide the features associated with the "Home Use" of system 232. For example, the downloaded application(a) may provide a calibration procedure to be performed on system 232 that enable system 232 to be operated to measure various angles related to patient 235 and humeral angles assumed by patient 235 as part of a motion measurement process. In some examples, the patient's arm when in the position shown in FIG. 18A is considered to be the relaxed at the patient's side position, having an angle 246 relative to the side of the patient. In some examples, this arm position and the measured angle 246 may be used as the "zero" point, using a measured value for angle 246, at least in as a part of the calibration procedure for system 232 when operating in the "Home Use" configuration.

Once system 232 has downloaded the appropriate application(s) and has been calibrated, patient 235 may run the applications to provide various features and functions related to taking measurements associated with humeral angles of the patient's arm or arms. In operation, system 232 may present patient 235, for example via a display of system 232, with the option to select a capture plane in which the patient wishes to capture humeral angle data. The display may also provide patient 235 with calibration and/or capture plane instructional information. Patient 235 may provide an indication, for example through actuation of an input provided by the display, indicating that the calibration is complete, and that the patient is ready to begin the process of capturing measurements. During capture of measurements, patient 235 may position the patient's arm to which system 232 is attached to different angles, such as at rest at the patient's side, and/or at thirty, sixty, ninety, and/or one hundred twenty degree angles.

In some examples, system 232 dynamically and automatically makes a measurement of the humeral angle as the patient moves the arm to which system 232 is attached. In other examples, the patient provides an input, such as actuation of an input provided to the display of system 232, or by a voice activated input, to indicate to system 232 that the patient's arm is in a position where the patient wishes the system to take an angle measurement. In various examples, the patient raises their arm in a series of repetitions between the at rest position and the maximum degree of elevation the patient can achieve, and system 232 automatically and dynamically measures and determines the maximum angle achieved for each rep. In various examples, patient 235 may indicate to system 232 that the patient has completed all the reps associated with that particular session. In various examples, system 232 is configured to allow patient 235 the ability to identify "windows" of range of motion where the patient 235 is experiencing pain, for example by pressing the display or a button of the electronic device of system 232 as they are raising or lowering their arm during a measurement procedure, or for example by a voice activated indication.

In some examples, following completion of a session, the patient 235 is offered an option, for example via the display of system 232, to email or otherwise communicate the results of the session to an authorized user associated with external devices 241, such as a physician or clinician. System 232 may also be configured to present the dynamically captured data for a session, for example using a graph displayed on the display of system 232. A list of the maximum elevations achieved in each rep of the session may also be provided as an output to the patient 235 via the display of system 232. Patient 235 may also be prompted for the option to participate in another session of reps and measurements, for example using the patient's opposite arm.

In various examples, following a session, system 232 and/or external devices 241 may be configured to compare the results, e.g., the progress or lack of progress, made during a given session with previous session(s), and can be configured to provide motivational messages to the client, to encourage the patient based on the most recent results, or based on a trend in the results over time. In some examples, these messages may be provided as outputs displayed on the display of system 232, and/or may be audible outputs, for example provided to a speaker or other audio output device (not shown in FIG. 18A-18B) included for example as part of the electronic device of system 232. Further, the capture and/or transmission of data related to patient 235 performing the reps described above may be associated with an exercise routine used as part of a therapy or treatment plan, wherein the capture of the data may provide a logging function for the patient and/or the user, such as the physician, clinician, or a physical therapist, who may be treating the patient, of the exercises themselves, and the progress resulting from the exercise routine.

FIG. 18D illustrates an example of patient 235 with the patient's arm having system 232 attached to it extended to a ninety-degree position, as indicated by angle 248. In various examples, this illustrates one possible position that patient 235 may assume as part of the "Home Use" of system 232 to measure humeral elevation angles during a session using any of the features and functions described above with respect to FIG. 18C.

While the examples illustrated and described throughout this disclosure may be applicable to shoulder and humeral motion measurements, the devices and techniques described herein may be applicable to other joint measurements, such as measurement associated with cervical and/or lumbar spine movements or movements of other limbs or bones of the body.

Figure 19:
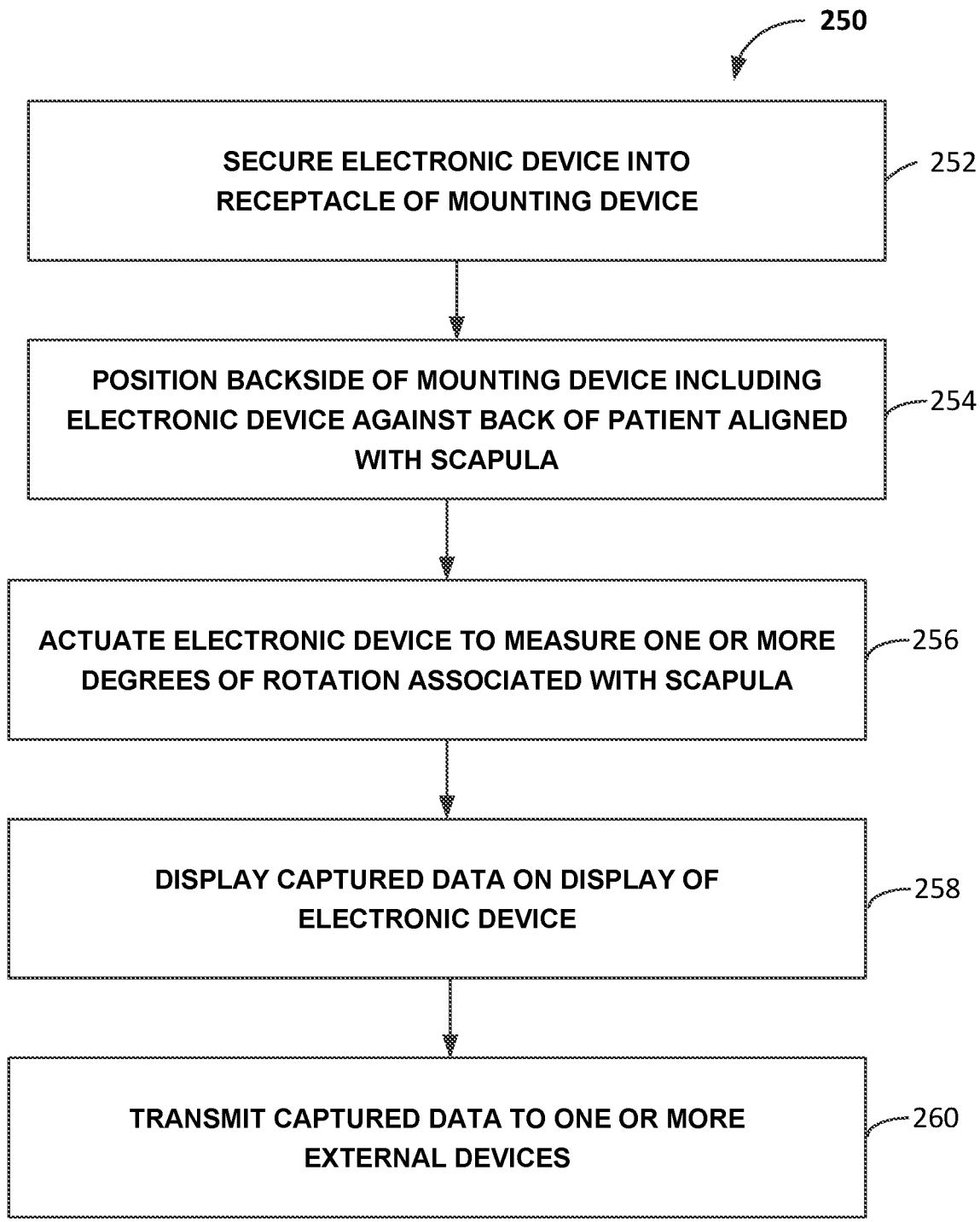
FIG. 19 illustrates a flowchart of a method according to various examples described in this disclosure.

FIG. 19 illustrates a flowchart of a method 250 according to various examples described in this disclosure. Although method 250 is described as being performed by system 10 as illustrated and described with respect to FIGS. 1A-1E, method 250 is not limited to being performed by any particular device or devices, and may be performed by any device or devices configured to perform the functions of method 250, including devices and systems as otherwise described herein. According to method 250, an electronic device 16 is secured into a receptacle 20 of a mounting device 12 (block 252). In some examples, electronic device 16 may have previously had one or more shoulder motion measurement applications, as described throughout this disclosure, downloaded to circuitry 18 included within electronic device 16. In some examples, the one or more shoulder motion measurement applications may be downloaded to electronic device 16 after electronic device 16 is secured in receptacle 20 of mounting device 12. In various examples, securing electronic device 16 into receptacle 20 includes calibration of electronic device 16 using any of the calibration procedures described in this disclosure, and/or any calibration procedure arranged to configure the electronic device 16 to perform the measurement functions ascribed to system 10.

Method 250 further includes positioning a backside of the mounting device 12 including the electronic device 16 against the back of a patient, the positioning aligning the system with a right or left scapula of a patient (block 256). Aligning the system to a scapula of the patient may be performed using any of the alignment procedures described throughout this disclosure, and any equivalents thereof.

Method 250 includes actuating electronic device 16 to measure one or more degrees of rotation associated with the scapula of the patient that has the system 10 aligned to that scapula (block 256). In various examples, actuation of the electronic device 16 includes receiving an indication of a touch, for example by a user, to the display 17 of electronic device 16. In various examples, measuring the one or more degrees of rotation associated with the scapula includes using one or more motion sensors included in electronic device 16, (such as any of the motion detection sensors included in motion detection unit 124 shown and illustrated for electronic device 120 in FIG. 9), to sense positional and/or orientation information associated with electronic device 16 at the time the indication of the actuation is received. In various examples, measuring one or more degrees of rotation associated with the scapula of the patient include receiving and processing, for example using one or more processors including in electronic device 16 (such as microprocessor 121 shown in FIG. 9), the signal generated by the one or more sensors to capture and store data corresponding to the measurements of the patient's scapula.

Method 250 may include display of the captured data on a display 17 of electronic device 16, for example using one or more user interface screens as described throughout this disclosure, and/or any equivalents thereof. In various examples, display of the captured data includes display of additional information, such as patient identification number and/or date and time information associated with the captured data. In various examples, information displayed may include data displayed in a tabular format, and/or data displayed in a graphical format.

Method 250 may include transmitting the captured data and/or other information associated with the patient and/or shoulder measurement information to one or more external devices, such as external devices 29 as shown in FIG. 1A. In various examples, the one or more external devices may be used to display and/or to further process and/or store the transmitted data for further analysis, for recording purposes, and/or for analysis by authorized users who may not be located at the same physical location as the patient at least at the time the measurements were taken.

Figure 20:
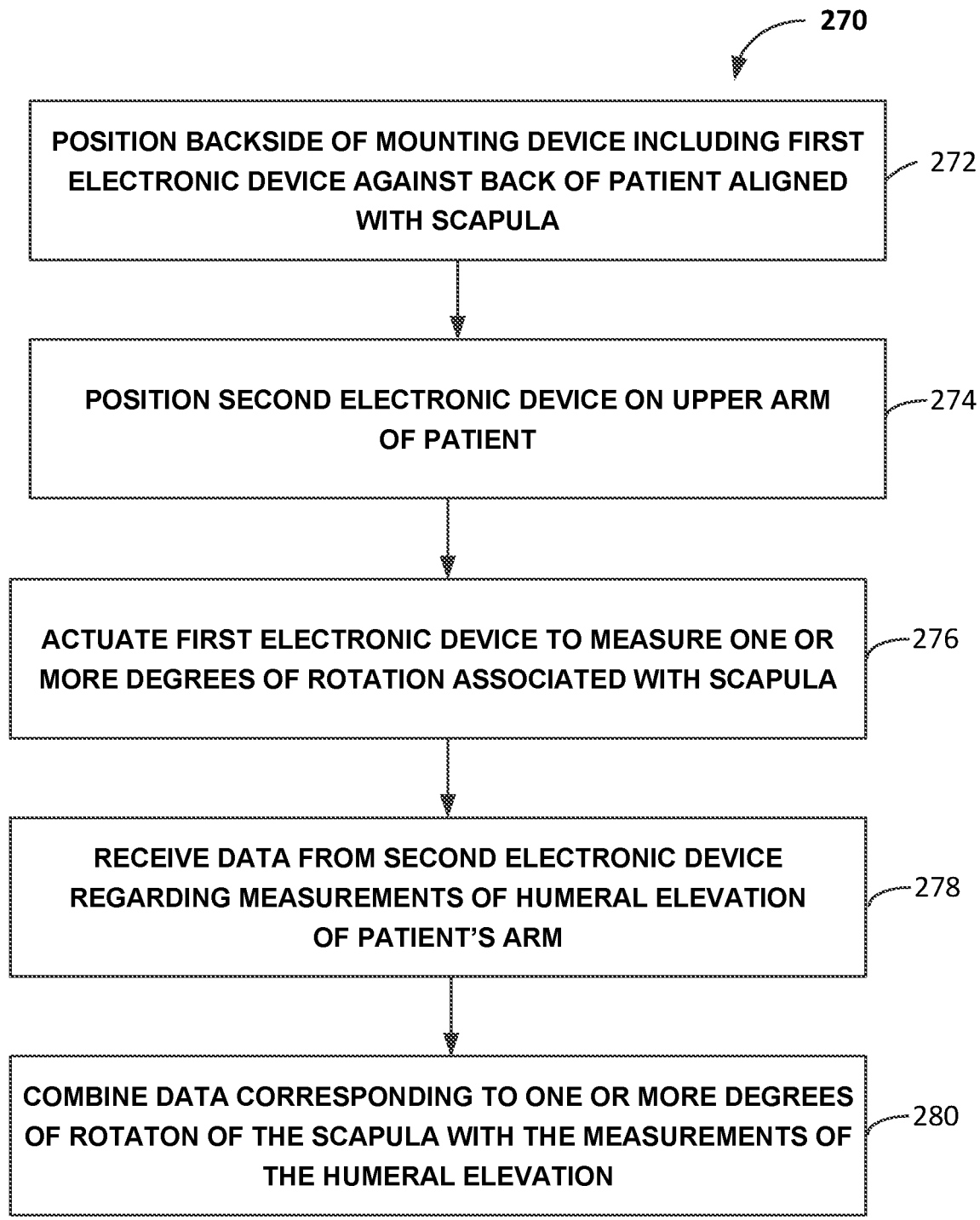
FIG. 20 illustrates a flowchart of another method according to various examples described in this disclosure.

FIG. 20 illustrates a flowchart of a method 270 according to various examples described in this disclosure. Although method 270 is described as being performed by system 231 and system 232 as illustrated and described with respect to FIGS. 18A-18B, method 270 is not limited to being performed by any particular device or devices, and may be performed by any device or devices configured to perform the functions of method 270, including devices and systems as otherwise described herein.

Method 270 includes positioning the backside of the mounting device 12 including a first electronic device, such as electronic device 16, of system 231 against the back of a patient, the positioning aligning the system with a right or left scapula of a patient (block 272). Positioning the mounting device 12 of system 231 including the first electronic device to a scapula of the patient may be performed using any of the alignment procedures described throughout this disclosure, and any equivalents thereof. In some examples, positioning system 231 includes securing the first electronic device 16 into a receptacle 20 of a mounting device 12. In some examples, the first electronic device of system 231 may have previously had one or more shoulder motion measurement applications, as described throughout this disclosure, downloaded to circuitry 18 included within the first electronic device. In some examples, the one or more shoulder motion measurement applications may be downloaded to the first electronic device after the first electronic device is secured in receptacle 20 of mounting device 12. In various examples, securing the first electronic device into receptacle 20 includes calibration of the first electronic device using any of the calibration procedures described in this disclosure, and/or any calibration procedure arranged to configure the first electronic device to perform the measurement functions ascribed to system 10.

Method 270 includes positioning a second system 232, including a second electronic device, such as electronic device 16, on the upper arm of the patient (block 274). Securing system 232 including the second electronic device to the upper arm of the patient includes securing system 232 to the arm of the patient on a same side, e.g., the right side or the left side, that corresponds to the same side of the patient where system 231 is positioned and aligned to the patient's right or left scapula. In some examples, the second electronic device of the system 232 may have previously had one or more shoulder motion measurement applications, as described throughout this disclosure, downloaded to circuitry 18 included within the second electronic device included in system 232. In some examples, the one or more shoulder motion measurement applications may be downloaded to the second electronic device after the second electronic device is secured to the patient. In various examples, securing the second electronic device to the patient includes calibration of the second electronic device using any of the calibration procedures described in this disclosure, and/or any calibration procedure arranged to configure the second electronic device to perform the measurement functions ascribed to system 230. In various examples, the second electronic device is configured to measure a humeral elevation angle associated with the position of the patient's arm to which system 232 is attached. In various examples, positioning of the second electronic device includes synchronizing the second electronic device to the first electronic device of system 231 so that the first and second electronic devices can communicate with one another in the process of taking measurements related to the scapula and/or arm positions of the patient.

Method 270 includes actuating the first electronic device to measure one or more degrees of rotation associated with the scapula of the patient (block 276). Actuating the first electronic device of system 231 in some examples triggers first electronic device to take measurements, using one or more of the measurement devices and techniques described throughout this disclosure or any equivalents thereof, related to the scapula of the patient to which system 231 is aligned. In addition, system 231 may communicate with system 232, requesting that system 232 make measurements, and in some examples to process these measurements to determine the current value for an angle associated with the orientation of the arm of the patient to which system 232 is attached. Upon receiving the request to take measurements, system 232 may be configured to sense a position/orientation of the second electronic device included in system 232, and thus the angle measurement requested by system 231. System 232 is then configured to automatically transmit data related to the measured position/orientation of the patient's arm back to system 231.

Method 270 includes system 232 receiving the information transmitted by system 232 (block 278). In various examples, the received information includes data regarding measurement(s) of humeral elevation(s) of the patient's arm at the time the request to take measurements was received by system 232.

Method 270 includes combining the data corresponding to the one or more degrees of rotation of the scapula with the received data transmitted by system 232 related to the humeral elevation measurement(s) as provided by system 232 (block 280).

In various examples, method 270 may further include any variation(s) of the display of the combined data in a similar manner as described above with respect to block 258 of method 250 in FIG. 19. In various examples, method 270 as illustrated in FIG. 20 may include transmitting the combined data, or some portion of the measured data from system 231 and/or system 232, to one or more external device(s) in a manner similar to that described above with respect to block 260 of method 250 in FIG. 19.

EXPERIMENTAL RESULTS

Instrument measurement accuracy compared to a non-human reference criterion has been investigated. This measures the accuracy of the device and application(s) only, and does not account for any human errors in palpation or placement of the mounting device on the scapula, or in positioning the arm. The results indicate that the values recorded by the mobile application are accurate relative to known values. Additionally, the upward rotation measurements do not appear affected by off axis rotations ($r^2<0.001$ for upward rotation with a 30-degree offset). This is a benefit of using the shoulder motion measurement system with 3D smartphone sensors as opposed to gravity based sensors (such as inclinometers). Inclinometers may display incorrect measurements when the movement being measured is no longer in the same plane as gravity. The accuracy testing also does not account for combinations of off axis errors, or repositioning of the device without recalibration. Additional filtering and processing algorithms may be added to improve accuracy under clinically robust conditions.

During the testing, the smartphone was manually held in position on a flat surface dependent of the angle being measured such that as a digital angle finder (the reference criterion) was tilted up, the primary motion was about the angle of interest (tilt, internal rotation or upward rotation). For the 30 degree off-set during upward rotation, the phone was held manually against a known angle of 30 degrees relative to gravity as the flat surface was tilted.

The following table summarizes accuracy as determined from the experiment:

| Instrument Accuracy of shoulder motion measurement system Mobile Application | | | | |
|---|---|---|---|---|
| Scapular Motion | $r^2$ | p-value | RMS error (degrees) | Denominator Degrees of Freedom |
| Upward rotation | 0.99 | <.0001 | 0.2 | 49 |
| Upward Rotation with 30 degree offset from gravity | 0.99 | <.0001 | 0.2 | 15 |
| Internal rotation | 0.99 | <.0001 | 0.2 | 49 |
| Tilt | 0.99 | <.0001 | 0.4 | 55 |

$r^2$, regression coefficient;
RMS, root mean square

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may be implemented, at least in part, in hardware, software, firmware or any combination thereof. For example, various aspects of the techniques may be implemented within processing circuitry such as one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described. These and other examples are within the scope of the following claims.

What is claimed is:

1. A non-transitory computer-readable medium comprising instructions that, when executed, cause one or more processors of an electronic computing device to:

receive, from a sensor of the electronic computing device, one or more sensor signals representing an orientation of a scapula of a patient for a plurality of positions corresponding to a 3-D motion of the scapula, the sensor signals generated by the sensor while the electronic computing device is positioned against the scapula of the patient;

generate, from the sensor signals, measured values for the orientation of the scapula, wherein the measured values comprise an upward rotation angle of the scapula, an internal rotation of the scapula, and a scapular tilt angle for one or more arm positions of the patient; and control a display of the electronic computing device to display a representation of the measured values for the upward rotation angle of the scapula, the internal rotation of the scapula, and the scapular tilt angle.

2. The non-transitory computer-readable medium of claim 1, wherein the electronic computing device comprises a first electronic computing device, and wherein the non-transitory computer-readable medium further comprises instructions that, when executed, cause the one or more processors to:
receive an input indicating a request to take measurements related to the scapula;
receive, from at least the sensor, the sensor signals representing the orientation of the scapula;
control a wireless transmitter circuit to transmit a request to a second electronic computing device positioned against an arm of the patient requesting that the second electronic computing device determine a measured value for a humeral elevation angle of the arm of the patient while the second electronic computing device is positioned against the arm of the patient;
control a wireless receiver to receive, from the second electronic computing device, data corresponding to the measured value for the humeral elevation angle;
combine the measured values for the orientation of the scapula with the measured value for the humeral elevation angle; and
control the display of the first electronic computing device to display the representation the measured values for the orientation of the scapula with the measured value for the humeral elevation angle.

3. The non-transitory computer-readable medium of claim 1, wherein the instructions, when executed, cause the one or more processors to:
receive a calibration input signal from at least the sensor for a plurality of positions along the 3-D motion of the scapula; and
perform a calibration process on at least the sensor in response to receiving the calibration input signal.

4. The non-transitory computer-readable medium of claim 1, wherein the sensor comprises an inertial measurement unit (IMU), and wherein the computer readable-medium further comprises instructions that, when executed, cause the one or more processors to:
receive user input indicating that the sensor of the electronic computing device is manually positioned against the scapula of the patient;
control the sensor to measure a relative position and a relative orientation of the scapula in response to receiving the user input;
control the sensor to output sensor data indicative of the relative position and the relative orientation of the scapula;
receive the sensor data; and
determine, based on the sensor data, one or more degrees of rotation comprising the upward rotation angle of the scapula, the internal rotation of the scapula, and the scapular tilt angle.

5. The non-transitory computer-readable medium of claim 4, further comprising instructions that, when executed, cause the one or more processors to:
control the IMU to measure a first relative position and a first relative orientation of the scapula while an arm of the patient is in a first position;
control the IMU to measure a second relative position and a second relative orientation of the scapula while the arm is in a second position; and
determine, based on the first relative position, the first relative orientation, the second relative position, and the second relative orientation of the scapula, the one or more degrees of rotation comprising the upward rotation angle of the scapula, the internal rotation of the scapula, and the scapular tilt angle.

6. The non-transitory computer-readable medium of claim 4, further comprising instructions that, when executed, cause the one or more processors to:
control the IMU to measure a change in relative position and relative orientation during a motion of an arm of the patient; and
determine, based on the change in relative position and relative orientation, the one or more degrees of rotation comprising the upward rotation angle of the scapula, the internal rotation of the scapula, and the scapular tilt angle.

7. The non-transitory computer-readable medium of claim 4, wherein the IMU comprises a first IMU, wherein the sensor data comprises first sensor data, and wherein the instructions, when executed, further cause the one or more processors to:
cause a second IMU secured to an arm of the patient to measure a humeral elevation angle of the arm;
cause the second IMU to output second sensor data comprising the humeral elevation angle;
receive the second sensor data; and
store in memory the second first sensor data in association with the second sensor data.

8. The non-transitory computer-readable medium of claim 4, wherein the instructions are further configured to cause the one or more processors to:
receive user input comprising a client identification number;
retrieve, based on the client identification number, a respective client profile from memory; and
store the one or more degrees of rotation comprising the upward rotation angle of the scapula, the internal rotation of the scapula, and the scapular tilt angle in the client profile.

9. The computer-readable medium of claim 8, further comprising instructions that, when executed, cause the one or more processors to monitor, based on the client profile, a change in the one or more degrees of rotation comprising the upward rotation angle of the scapula, the internal rotation of the scapula, and the scapular tilt angle over time.

10. The computer-readable medium of claim 4, further comprising instructions that, when executed, cause the one or more processors to output the one or more degrees of rotation comprising the upward rotation angle of the scapula, the internal rotation of the scapula, and the scapular tilt angle for display on the display of the electronic computing device.

11. The computer-readable medium of claim 4, further comprising instructions that, when executed, cause the one or more processors to determine, based on the one or more degrees of rotation, a classification category for the one or more degrees of rotation comprising the upward rotation angle of the scapula, the internal rotation of the scapula, and the scapular tilt angle.

12. The computer-readable medium of claim 11, further comprising instructions that, when executed, cause the one or more processors to determine, based on the classification category, a shoulder-movement disorder of the patient.

13. The computer-readable medium of claim 4, further comprising instructions that, when executed, cause the one or more processors to determine, based on the shoulder-movement disorder, a recommended therapy.

14. A non-transitory computer-readable storage medium having stored thereon instructions that, when executed, cause processing circuitry to:
- receive an input signal indicating that an electronic computing device manually positioned against and aligned to a scapula of a patient is to take one or more measurements corresponding to an orientation of the scapula of the patient for a plurality of positions corresponding to a 3-D motion of the scapula;
- control one or more sensors within the electronic computing device to generate sensor output signals corresponding to the one or more measurements corresponding to the orientation of the scapula of the patient for one or more arm positions of the patient;
- receive the generated sensor output signals;
- generate, based on the sensor output signals, measured values for the orientation of the scapula, wherein the measured values comprise an upward rotation angle of the scapula, an internal rotation of the scapula, and a scapular tilt angle; and
- control a display of the electronic computing device to display a representation of the measured values for the upward rotation angle of the scapula, the internal rotation of the scapula, and the scapular tilt angle.

15. The non-transitory computer-readable storage medium of claim 14, wherein the electronic computing device comprises a first electronic computing device, and wherein the instructions, when executed, cause the processing circuitry to:
- control a transmitter circuit of the first electronic computing device to transmit a communication to a second electronic computing device secured to an arm of the patient that causes the second electronic computing device to measure a humeral elevation angle of the arm of the patient;
- receive, via a receiver circuit of the first electronic computing device, a signal from the second electronic computing device that includes data corresponding to the humeral elevation angle measured by the second electronic computing device in response to the communication; and
- combine the measured values for the upward rotation angle of the scapula, the internal rotation of the scapula, and the scapular tilt angle with the received data corresponding to the humeral elevation angle so that the measured values for the orientation of the scapula correspond to a particular value of the humeral elevation angle.

16. A method comprising:
- receiving, from a sensor of an electronic computing device, one or more sensor signals representing an orientation of a scapula of a patient for a plurality of positions corresponding to a 3-D motion of the scapula, the sensor signals generated by the sensor while the electronic computing device is positioned against the scapula of the patient;
- generating, from the sensor signals, measured values for the orientation of the scapula, wherein the measured values comprise an upward rotation angle of the scapula, an internal rotation of the scapula, and a scapular tilt angle for one or more arm positions of the patient; and
- controlling a display of the electronic computing device to display a representation of the measured values for the upward rotation angle of the scapula, the internal rotation of the scapula, and the scapular tilt angle.

17. The method claim 16, wherein the electronic computing device comprises a first electronic computing device, and wherein the method further comprises:
- receiving an input indicating a request to take measurements related to the scapula; receiving, from at least the sensor, the sensor signals representing the orientation of the scapula;
- controlling a wireless transmitter circuit to transmit a request to a second electronic computing device positioned against an arm of the patient requesting that the second electronic computing device determine a measured value for a humeral elevation angle of an arm of the patient while the second electronic computing device is positioned against the arm of the patient;
- controlling a wireless receiver to receive, from the second electronic computing device, data corresponding to the measured value for the humeral elevation angle;
- combining the measured values for the orientation of the scapula with the measured value for the humeral elevation angle; and
- controlling the display of the first electronic computing device to display the one or more representations for the measured values for the orientation of the scapula with the measured value for the humeral elevation angle.

* * * * *